(12) United States Patent
Atkinson et al.

(10) Patent No.: US 8,486,687 B2
(45) Date of Patent: Jul. 16, 2013

(54) SPORULATION-DEFICIENT THERMOPHILIC MICROORGANISMS FOR THE PRODUCTION OF ETHANOL

(75) Inventors: Anthony Atkinson, Guildford (GB); Roger Cripps, Guildford (GB); Kirstin Eley, Guildford (GB)

(73) Assignee: TMO Renewables Limited, Guildford, Surrey (GB)

( * ) Notice: Subject to any disclaimer, the term of this patent is extended or adjusted under 35 U.S.C. 154(b) by 0 days.

(21) Appl. No.: 13/127,927

(22) PCT Filed: Nov. 5, 2009

(86) PCT No.: PCT/GB2009/051487
§ 371 (c)(1),
(2), (4) Date: May 13, 2011

(87) PCT Pub. No.: WO2010/052499
PCT Pub. Date: May 14, 2010

(65) Prior Publication Data
US 2011/0217760 A1    Sep. 8, 2011

(30) Foreign Application Priority Data
Nov. 5, 2008   (GB) .................................. 0820262.4

(51) Int. Cl.
| C12N 1/20 | (2006.01) |
| C12N 15/00 | (2006.01) |
| C12N 1/00 | (2006.01) |
| C12N 9/00 | (2006.01) |
| C12N 9/02 | (2006.01) |
| C12N 9/04 | (2006.01) |
| C12N 9/10 | (2006.01) |
| C12Q 1/00 | (2006.01) |
| C12Q 1/68 | (2006.01) |
| C07H 21/04 | (2006.01) |

(52) U.S. Cl.
USPC .................. 435/252.31; 435/440; 435/320.1; 435/252.3; 435/243; 435/183; 435/189; 435/190; 435/193; 435/4; 435/6.1; 536/23.2

(58) Field of Classification Search
None
See application file for complete search history.

(56) References Cited

U.S. PATENT DOCUMENTS

| 5,238,833 A | 8/1993 | Sanders et al. |
| 5,589,369 A | 12/1996 | Seidman et al. |
| 6,664,076 B2 | 12/2003 | Green et al. |
| 7,691,620 B2 | 4/2010 | Green et al. |
| 8,021,865 B2 | 9/2011 | Atkinson et al. |
| 2002/0034816 A1 | 3/2002 | Green et al. |
| 2008/0305536 A1 | 12/2008 | Atkinson et al. |
| 2009/0042265 A1 | 2/2009 | Atkinson et al. |
| 2009/0197314 A1 | 8/2009 | Atkinson et al. |
| 2010/0173373 A1 | 7/2010 | Atkinson et al. |
| 2011/0318802 A1 | 12/2011 | Atkinson et al. |

FOREIGN PATENT DOCUMENTS

| EP | 0124076 A2 | 11/1984 |
| EP | 0351717 A2 | 1/1990 |
| EP | 0 937 774 A1 | 8/1999 |
| FR | 2 477 572 A1 | 9/1981 |
| GB | 2 074 188 A | 8/1981 |
| GB | 2171703 A | 9/1986 |
| JP | 2005-261239 A | 9/2005 |
| WO | WO 88/09379 A2 | 12/1988 |
| WO | WO 98/45425 A1 | 10/1998 |
| WO | WO 01/49865 A1 | 7/2001 |
| WO | WO 01/83784 A2 | 11/2001 |
| WO | WO 02/29030 A3 | 4/2002 |
| WO | WO 2006/117536 A1 | 11/2006 |
| WO | WO 2006/131734 A1 | 12/2006 |
| WO | WO 2007/039753 A1 | 4/2007 |
| WO | WO 2008/038019 A3 | 4/2008 |
| WO | WO 2009/022158 A1 | 2/2009 |

OTHER PUBLICATIONS

Rowe-Magnus et al. Identification of a second region of the Spo0A response regulator of *Bacillus subtilis* required for transcription activation. J Bacteriol. Aug. 2000;182(15):4352-5.*
Lewis et al. Domain swapping in the sporulation response regulator Spo0A. J Mol Biol. Mar. 31, 2000;297(3):757-70.*
UnitProt Database—*Geobacillus* Lactate Dehydrogenase. Retrived from the internet on Mar. 22, 2012 via http://www.uniprot.org/uniprot/?query=geobacillus++lactate+dehydrogenase&sort=score.*
UnitProt Database—*Geobacillus* spo0A. Retrived from the internet on Mar. 22, 2012 via http://www.uniprot.org/uniprot/?query=geobacillus+spo0a&sort=score.*
NCBI Database—*Geobacillus*. Retrieved from the internet on Mar. 22, 2012 via http://www.ncbi.nlm.nih.gov/Taxonomy/Browser/wwwtax.cgi?id=129337.*
Fong, J. C. N. et al. "Isolation and characterization of two novel ethanol-tolerant facultative-anaerobic thermophilic bacteria strains from waste compost" *Extremophiles*, Mar. 2006, 10:363-372.
Kuisiene, N. et al. "Phylogenetic, Inter, and Intraspecific Sequence Analysis of *spo0A* Gene of the Genus *Geobacillus*" *Curr Microbiol*, Feb. 2009, 58:547-553.
Lee, D. H. et al. "Ethanol Fermentation of Corn Starch by a Recombinant *Saccharomyces cerevisiae* Having Glucaomylase and α-Amylase Activities" *J. Food Sci. Nutr.*, 2001, 6(4):206-210.
Molle, V. et al. "The Spo0A regulon of *Bacillus subtilis*" *Molecular Microbiology*, 2003, 50(5):1683-1701.
Payton, M. A. "Production of ethanol by thermophilic bacteria" *Trends in Biotechnology*, 1984, 2(6):153-158.
Stephenson, K. et al. "Molecular insights into the initiation of sporulation in Gram-positive bacteria: new technologies for an old phenomenon" *FEMS Microbiology Reviews*, 2005, 29:281-301.

(Continued)

*Primary Examiner* — Yong Pak
(74) *Attorney, Agent, or Firm* — Saliwanchik, Lloyd & Eisenschenk

(57) ABSTRACT

A thermophilic microorganism comprising a modification that prevents sporulation, wherein the modification inactivates the native spo0A gene.

18 Claims, 8 Drawing Sheets

OTHER PUBLICATIONS

Barstow, D.A. et al. "Cloning, expression and complete nucleotide sequence of the *Bacillus stearothermophilus* L-lactate dehydrogenase gene" Gene, 1986, 46:47-55, abstract.

Biswas, I. et al. "High-Efficiency Gene Inactivation and Replacement System for Gram-Positive Bacteria," Journal of Bacteriology, Jun. 1, 1993, pp. 175(11):3628-3635, Washington, DC, US, XP000563688.

Breuer, M. et al. "High-throughput assay of (R)-phenylacetylcarbinol synthesized by pyruvate decarboxylase" Anal Bioanal Chem, 2002, 374:1069-1073.

Carlsson, J. et al. "Pyruvate Dehydrogenase Activity in *Streptococcus mutans*" Infection and Immunity, 1985, 49(3):674-678.

Database WPI Week 200567, Thomson Scientific, AN 2005-653380, XP002487167 & JP2005-261239A, Sep. 29, 2005.

Desai, S.G. et al. "Cloning of L-lactate dehydrogenase and elimination of lactic acid production via gene knockout in Thermoanaerobacterium saccharolyticum JW/SL-YS485," Applied Microbiology and Biotechnology, Oct. 2004, 65(5):600-605, XP002393736.

Fortina, M.G. et al. "Reclassification of Saccharococcus caldoxylosilyticus as *Geobacillus* caldoxylosilyticus (Ahmad et al. 2000) comb nov" International Journal of Systematic and Evolutionary Microbiology, 2001, 51:2063-2071.

Gao, H. et al. "The E1β and E2 Subunits of the *Bacillus subtilis* Pyruvate Dehydrogenase Complex Are Involved in Regulation of Sporulation" Journal of Bacteriology, May 2002, 184(10):2780-2788.

*Geobacillus thermoglucosidasius*. NCBI Databases, pp. 1-3, printed from the internet on Oct. 29, 2010.

Germain, P. et al. "Ethanol production by anaerobic thermophilic bacteria: regulation of lactate dehydrogenase activity in *Clostridium thermohydrosulfuricum*" Appl Microbiol Biotechnol, 1986, 24:300-305.

Hartley, B.S. et al. (May 1983) "Development and Economics of a Novel Thermophilic Ethanol Fermentation" Presentations from Biotech '83 London, May 4-6, 1983 First World Conference, Biotech, Northwood, Online Conf. Ltd, GB, pp. 895-905.

Hollmann, R. et al. "Pyruvate formation and suppression in recombinant *Bacillus megaterium* cultivation" Journal of Biotechnology, 2004, 111:89-96.

Jimenez, J. et al."Selection of Ethanol-Tolerant Yeast Hybrids in pH-Regulated Continuous Culture" Applied and Environmental Microbiology, Apr. 1988, 54(4):917-922.

Larsen, L. et al. "*Thermoanaerobacter mathranii* sp. Nov., an ethanol-producing, extremely thermophilic anaerobic bacterium from a hot spring in Iceland" Arch Microbiol, 1997, 168:114-119.

Lessard, I.A.D. et al. "Expression in *Escherichia coli* of Genes Encoding the E1α and E1β Subunits of the Pyruvate Dehydrogenase Complex of *Bacillus stearothermophilis* and Assembly of a Functional E1 Component (α1β2) in Vitro" The Journal of Biological Chemistry, 1994, 269(14):10378-10383.

Lynd, L.R. et al. "Thermophilic Ethanol Production: Investigation of Ethanol Yield and Tolerance in Continuous Culture" Applied Biochemistry and Biotechnology, 1991, 28/29:549-570.

Neveling, U. et al. "Gene and subunit organization of bacterial pyruvate dehydrogenase complexes" Biochemica et Biophysica Acta, 1998, 1385:367-372.

Nichols, N.N. et al. "Engineering lactic acid bacteria with pyruvate decarboxylase and alcohol dehydrogenase genes for ethanol production from *Zymomonas mobilis*" J Ind Microbiol Biotechnol, 2003, 30:315-321.

Niu, X.D. et al. "Cloning and nucleotide sequence of the gene for dihydrolipoamide acetyltransferase from *Saccharomyces cerevisiae*" Proc. Natl. Acad. Sci. USA, Oct. 1988, 85:7546-7550.

San Martin, R. et al. "Development of a synthetic medium for continuous anaerobic growth and ethanol production with a lactate dehydrogenase mutant of *Bacillus stearothermophilus*," Journal of General Microbiology, Feb. 3, 1992, 138:987-996, Great Britain.

San Martin, R. et al. "Pathways of ethanol production from sucrose by a mutant thermophilic *Bacillus* in continuous culture," Journal of General Microbiology, Jan. 5, 1993, 139:1033-1040, Great Britain.

Schütz, A. et al. "Crystal structure of thiamindiphosphate-dependent indolepyruvate decarboxylase from *Enterobacter cloacae*, an enzyme involved in the biosynthesis of the plant hormone indole-3-acetic acid" Eur. J. Biochem., 2003, 270:2312-2321.

Schütz, A. et al. "Studies on structure-function relationships of indolepyruvate decarboxylase from *Enterobacter cloacae*, a key enzyme of the indole acetic acid pathway" Eur. J. Biochem., 2003, 270:2322-2331.

Siegert, P. et al. "Exchanging the substrate specificities of pyruvate decarboxylase from *Zymomonas mobilis* and benzoylformate decarboxylase from *Pseudomonas putida*" Protein Engineering, Design & Selection, 2005, 18(7):345-357.

Tomar, A. et al. "The effect of acetate pathway mutations on the production of pyruvate in *Escherichia coli*" Appl Microbiol Biotechnol, 2003, 62:76-82.

Wendisch, V.F. et al. "Metabolic engineering of *Escherichia coli* and *Corynebacterium glutamicum* for biotechnological production of organic acids and amino acids" Current Opinion in Microbiology, 2006, 9:268-274.

Witzmann, S. et al. "The pyruvate dehydrogenase complex from the thermophilic organisms: thermal stability and re-association from the enzyme components" Biochemica et Biophysica Acta, 1998, 13885:341-352.

Yomano, L.P. et al. "Isolation and characterization of ethanol-tolerant mutants of *Escherichia coli* KO11 for fuel ethanol production" Journal of Industrial Microbiology & Biotechnology, Feb. 1998, 20(2):132-138.

Office Action dated May 5, 2010 in U.S. Appl. No. 11/915,930, filed Sep. 29, 2008.

Office Action dated Nov. 15, 2010 in U.S. Appl. No. 11/915,930, filed Sep. 29, 2008.

Office Action dated Nov. 17, 2009 in U.S. Appl. No. 11/913,480, filed Apr. 17, 2008.

Office Action dated Jun. 25, 2010 in U.S. Appl. No. 11/913,480, filed Apr. 17, 2008.

Office Action dated Jun. 16, 2011 in U.S. Appl. No. 12/066,526, filed Jun. 29, 2008.

Office Action dated Feb. 18, 2011 in U.S. Appl. No. 12/066,526, filed Jun. 29, 2008.

Office Action dated Mar. 7, 2011 in U.S. Appl. No. 12/376,826, filed May 22, 2009.

De Graef, M.R. et al. "The Steady-State Internal Redox State (NADH/NAD) Reflects the External Redox State and Is Correlated with Catabolic Adaptation in *Escherichia coli*" J. Bacterial., Apr. 1999, 181(8):2351-2357.

Lapierre, L. et al. "D-Lactate Dehydrogenase Gene (ldhD) Inactivation and Resulting Metabolic Effects in the *Lactobacillus johnsonii* Strains La1 and N312" Appl. Environ. Microbiol., Sep. 1999, 65(9):4002-4007.

Nakajima, R. et al. "Nucleotide Sequence of the *Bacillus stearothermophilus* α-Amylase Gene" J. Bacteriol., Jul. 1985, 163(1):401-406.

Office Action dated Sep. 23, 2011 in U.S. Appl. No. 12/376,826, filed May 22, 2009.

Office Action dated Oct. 14, 2011 in U.S. Appl. No. 13/191,056, filed Jul. 26, 2011.

\* cited by examiner

TTGGGAGTAAGGGGGAAGGTTTTCTTGAAAATTAAAGTATGTATTGCGGACGATAACCGT
GAGTTAGTGAATTTGCTCGAAGAATATATTTCCAGCCAAAGCGACATGGAAGTGATCGGG
ACTGCTTATAATGGCCAAGATTGCTTATATATGCTCGAGGAAAAACAACCGGATGTGTTA
TTGTTAGACATTATTATGCCTCATTTAGATGGATTGGCCGTATTGGAAAAAATTCGTGCG
AAGCGGGAAAAACAACCGAGCGTGATCATGCTGACAGCATTTGGCCAAGAAGATGTAACG
AAAAAAGCGGTTGAACTTGGCGCCTCTTATTTTATTTTAAAACCGTTTGACATGGAAAAT
TTAGTGTATCATATCCGCCAAGTGCATGGAAAAACGGCACCAATGGTGAAAAAAGCGGCG
TCTGCCTACCAAACGCGGGATAACAGGCCGAAAAATCTGGACGCAAGCATTACGAGCATC
ATTCATGAAATCGGCGTTCCGGCGCATATTAAAGGATATTTATATTTACGTGAAGCGATC
GCCATGGTGTATAACGATATTGAATTGCTCGGCGCAATTACGAAAGTGCTTTACCCGGAC
ATTGCCAAAAAATATAACACAACGGCCAGCCGTGTCGAGCGGGCGATCCGCCATGCGATT
GAAGTCGCTTGGAGCCGCGGCAATCTCGAATCGATTTCTTCCTTATTCGGCTACACCGTC
AGCGTGTCGAAAGCCAAACCGACAAACAGCGAATTCATCGCGATGGTCGCCGATAAGTTA
AGATTAGAGCATAAAGCTTCTTAA

FIGURE 1

MGVRGKVFLKIKVCIADDNRELVNLLEEYISSQSDMEVIGTAYNGQDCLYMLEEKQPDVL
LLDIIMPHLDGLAVLEKIRAKREKQPSVIMLTAFGQEDVTKKAVELGASYFILKPFDMEN
LVYHIRQVHGKTAPMVKKAASAYQTRDNRPKNLDASITSIIHEIGVPAHIKGYLYLREAI
AMVYNDIELLGAITKVLYPDIAKKYNTTASRVERAIRHAIEVAWSRGNLESISSLFGYTV
SVSKAKPTNSEFIAMVADKLRLEHKAS

FIGURE 2

Lane 1: #7 (in-frame)
Lane 2: #9 (out-of-frame)
Lane 3: #13 (out-of-frame)
Lane 4: #16 (wild-type)
Lane 5: TM242

SEQUENCE LISTING

<160> NUMBER OF SEQ ID NOS: 4

<210> SEQ ID NO 1
<211> LENGTH: 804
<212> TYPE: DNA
<213> ORGANISM: Geobacillus thermoglucosidasius

<400> SEQUENCE: 1

```
ttgggagtaa gggggaaggt tttcttgaaa attaaagtat gtattgcgga cgataaccgt      60
gagttagtga atttgctcga agaatatatt tccagccaaa gcgacatgga agtgatcggg     120
actgcttata atggccaaga ttgcttatat atgctcgagg aaaaacaacc ggatgtgtta     180
ttgttagaca ttattatgcc tcatttagat ggattggccg tattggaaaa aattcgtgcg     240
aagcgggaaa aacaaccgag cgtgatcatg ctgacagcat ttggccaaga agatgtaacg     300
aaaaaagcgg ttgaacttgg cgcctcttat tttattttaa aaccgtttga catggaaaat     360
ttagtgtatc atatccgcca agtgcatgga aaaacggcac caatggtgaa aaaagcggcg     420
tctgcctacc aaacgcggga taacaggccg aaaaatctgg acgcaagcat tacgagcatc     480
attcatgaaa tcggcgttcc ggcgcatatt aaaggatatt tatatttacg tgaagcgatc     540
gccatggtgt ataacgatat tgaattgctc ggcgcaatta cgaaagtgct ttacccggac     600
attgccaaaa aatataacac aacggccagc cgtgtcgagc gggcgatccg ccatgcgatt     660
gaagtcgctt ggagccgcgg caatctcgaa tcgatttctt ccttattcgg ctacaccgtc     720
agcgtgtcga aagccaaacc gacaaacagc gaattcatcg cgatggtcgc cgataagtta     780
```
agattagagc ataaagcttc ttaa                                                    804

<210> SEQ ID NO 2
<211> LENGTH: 267
<212> TYPE: PRT
<213> ORGANISM: Geobacillus thermoglucosidasius

<400> SEQUENCE: 2

```
Met Gly Val Arg Gly Lys Val Phe Leu Lys Ile Lys Val Cys Ile Ala
1               5                   10                  15

Asp Asp Asn Arg Glu Leu Val Asn Leu Leu Glu Glu Tyr Ile Ser Ser
            20                  25                  30

Gln Ser Asp Met Glu Val Ile Gly Thr Ala Tyr Asn Gly Gln Asp Cys
        35                  40                  45

Leu Tyr Met Leu Glu Glu Lys Gln Pro Asp Val Leu Leu Leu Asp Ile
    50                  55                  60

Ile Met Pro His Leu Asp Gly Leu Ala Val Leu Glu Lys Ile Arg Ala
65                  70                  75                  80

Lys Arg Glu Lys Gln Pro Ser Val Ile Met Leu Thr Ala Phe Gly Gln
                85                  90                  95

Glu Asp Val Thr Lys Lys Ala Val Glu Leu Gly Ala Ser Tyr Phe Ile
            100                 105                 110

Leu Lys Pro Phe Asp Met Glu Asn Leu Val Tyr His Ile Arg Gln Val
        115                 120                 125

His Gly Lys Thr Ala Pro Met Val Lys Lys Ala Ala Ser Ala Tyr Gln
    130                 135                 140

Thr Arg Asp Asn Arg Pro Lys Asn Leu Asp Ala Ser Ile Thr Ser Ile
145                 150                 155                 160

Ile His Glu Ile Gly Val Pro Ala His Ile Lys Gly Tyr Leu Tyr Leu
                165                 170                 175

Arg Glu Ala Ile Ala Met Val Tyr Asn Asp Ile Glu Leu Leu Gly Ala
            180                 185                 190

Ile Thr Lys Val Leu Tyr Pro Asp Ile Ala Lys Lys Tyr Asn Thr Thr
        195                 200                 205

Ala Ser Arg Val Glu Arg Ala Ile Arg His Ala Ile Glu Val Ala Trp
    210                 215                 220

Ser Arg Gly Asn Leu Glu Ser Ile Ser Ser Leu Phe Gly Tyr Thr Val
225                 230                 235                 240

Ser Val Ser Lys Ala Lys Pro Thr Asn Ser Glu Phe Ile Ala Met Val
                245                 250                 255

Ala Asp Lys Leu Arg Leu Glu His Lys Ala Ser
            260                 265
```

<210> SEQ ID NO 3
<211> LENGTH: 5082
<212> TYPE: DNA
<213> ORGANISM: Geobacillus thermoglucosidasius

<400> SEQUENCE: 3
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcgggctgg cttaactatg cggcatcaga gcagattgta ctgagagtgc    180
accatatatg cggtgtgaaa taccgcacag atgcgtaagg agaaaatacc gcatcaggcg   240
taaccaacat gattaacaat tattagaggt catcgttcaa atggtatgc gttttgacac     300 atccactata tatccgtgtc gttctgtcca ctcctgaatc ccattccaga aattctctag   360

```
cgattccaga agtttctcag agtcggaaag ttgaccagac attacgaact ggcacagatg    420
gtcataacct gaaggaagat ctgattgctt aactgcttca gttaagaccg aagcgctcgt    480
cgtataacag atgcgatgat gcagaccaat caacatggca cctgccattg ctacctgtac    540
agtcaaggat ggtagaaatg ttgtcggtcc ttgcacacga atattacgcc atttgcctgc    600
atattcaaac agctcttcta cgataagggc acaaatcgca tcgtggaacg tttgggcttc    660
taccgattta gcagtttgat acactttctc taagtatcca cctgaatcat aaatcggcaa    720
aatagagaaa aattgaccat gtgtaagcgg ccaatctgat tccacctgag atgcataatc    780
tagtagaatc tcttcgctat caaaattcac ttccaccttc cactcaccgg ttgtccattc    840
atggctgaac tctgcttcct ctgttgacat gacacacatc atctcaatat ccgaataggg    900
cccatcagtc tgacgaccaa gagagccata acaccaata gccttaacat catccccata    960
tttatccaat attcgttcct taatttcatg aacaatcttc attctttctt ctctagtcat   1020
tattattggt ccattcacta ttctcattcc cttttcagat aattttagat ttgcttttct   1080
aaataagaat atttggagag caccgttctt attcagctat taataactcg tcttcctaag   1140
catccttcaa tccttttaat aacaattata gcatctaatc ttcaacaaac tggcccgttt   1200
gttgaactac tctttaataa aataattttt ccgttcccaa ttccacattg caataataga   1260
aaatccatct tcatcggctt tttcgtcatc atctgtatga atcaaatcgc cttcttctgt   1320
gtcatcaagg tttaatttt tatgtatttc ttttaacaaa ccaccatagg agattaacct   1380
tttacggtgt aaaccttcct ccaaatcaga caaacgtttc aaattctttt cttcatcatc   1440
ggtcataaaa tccgtatcct ttacaggata ttttgcagtt tcgtcaattg ccgattgtat   1500
atccgattta tatttatttt tcggtcgaat catttgaact tttacatttg gatcatagtc   1560
taatttcatt gcctttttcc aaaattgaat ccattgtttt tgattcacgt agttttctgt   1620
attcttaaaa taagttggtt ccacacatac caatacatgc atgtgctgat tataagaatt   1680
atctttatta tttattgtca cttccgttgc acgcataaaa ccaacaagat ttttattaat   1740
ttttttatat tgcatcattc ggcgaaatcc ttgagccata tctgacaaac tcttatttaa   1800
ttcttcgcca tcataaacat ttttaactgt taatgtgaga acaaccaac gaactgttgg   1860 cttttgttta ataacttcag caacaacctt ttgtgactga atgccatgtt tcattgctct   1920
cctccagttg cacattggac aaagcctgga tttacaaaac cacactcgat acaactttct   1980
ttcgcctgtt tcacgatttt gtttatactc taatatttca gcacaatctt ttactctttc   2040
agccttttta aattcaagaa tatgcagaag ttcaaagtaa tcaacattag cgattttctt   2100
ttctctccat ggtctcactt ttccacttt tgtcttgtcc actaaaaccc ttgattttc   2160 atctgaataa atgctactat taggacacat aatattaaaa gaaaccccca tctatttagt   2220
tatttgttta gtcacttata actttaacag atggggtttt tctgtgcaac caattttaag   2280
ggttttcaat actttaaaac acatacatac caacacttca acgcacctt cagcaactaa    2340 aataaaaatg acgttattc tatatgtatc aagataagaa agaacaagtt caaaaccatc    2400
aaaaaaagac acctttcag gtgctttttt tattttataa actcattccc tgatctcgac    2460
ttcgttcttt ttttacctct cggttatgag ttagttcaaa ttcgttcttt ttaggttcta    2520
aatcgtgttt ttcttggaat tgtgctgttt tatcctttac cttgtctaca aacccttaa    2580 aaacgttttt aaaggctttt aagccgtctg tacgttcctt aaggaattaa ttcgccattc    2640
gccattcagg ctgcgcaact gttgggaagg gcgatcggtg cgggcctctt cgctattacg    2700
ccagctggcg aaaggggat gtgctgcaag gcgattaagt tgggtaacgc cagggttttc    2760
```

```
ccagtcacga cgttgtaaaa cgacggccag tgaattcgag ctcggtaccc ggggatcctc    2820
tagagtcgac ctgcaggcat gcaagcttgg cgtaatcatg gtcatagctg tttcctgtgt    2880
gaaattgtta tccgctcaca attccacaca catacgagc cggaagcata agtgtaaag      2940
cctggggtgc ctaatgagtg agctaactca cattaattgc gttgcgctca ctgcccgctt    3000
tccagtcggg aaacctgtcg tgccagctgc attaatgaat cggccaacgc gcggggagag    3060
gcggtttgcg tattgggcgc tcttccgctt cctcgctcac tgactcgctg cgctcggtcg    3120
ttcggctgcg gcgagcggta tcagctcact caaaggcggt aatacggtta tccacagaat    3180
caggggataa cgcaggaaag aacatgtgag caaaaggcca gcaaaaggcc aggaaccgta    3240
aaaaggccgc gttgctggcg ttttttccata ggctccgccc ccctgacgag catcacaaaa    3300
atcgacgctc aagtcagagg tggcgaaacc cgacaggact ataaagatac caggcgtttc    3360
ccccctggaag ctccctcgtg cgctctcctg ttccgaccct gccgcttacc ggatacctgt    3420
ccgcctttct cccttcggga agcgtggcgc tttctcatag ctcacgctgt aggtatctca    3480
gttcggtgta ggtcgttcgc tccaagctgg gctgtgtgca cgaacccccc gttcagcccg    3540
accgctgcgc cttatccggt aactatcgtc ttgagtccaa cccggtaaga cacgacttat    3600
cgccactggc agcagccact ggtaacagga ttagcagagc gaggtatgta ggcggtgcta    3660
cagagttctt gaagtggtgg cctaactacg gctacactag aagaacagta tttggtatct    3720
gcgctctgct gaagccagtt accttcggaa aaagagttgg tagctcttga tccggcaaac    3780
aaaccaccgc tggtagcggt ggtttttttg tttgcaagca gcagattacg cgcagaaaaa    3840
aaggatctca agaagatcct ttgatctttt ctacggggtc tgacgctcag tggaacgaaa    3900
actcacgtta agggattttg gtcatgagat tatcaaaaag gatcttcacc tagatccttt    3960
taaattaaaa atgaagtttt aaatcaatct aaagtatata tgagtaaact tggtctgaca    4020
gttaccaatg cttaatcagt gaggcaccta tctcagcgat ctgtctattt cgttcatcca    4080
tagttgcctg actccccgtc gtgtagataa ctacgatacg ggagggctta ccatctggcc    4140
ccagtgctgc aatgataccg cgagacccac gctcaccggc tccagattta tcagcaataa    4200
accagccagc cggaagggcc gagcgcagaa gtggtcctgc aactttatcc gcctccatcc    4260
agtctattaa ttgttgccgg gaagctagag taagtagttc gccagttaat agtttgcgca    4320
acgttgttgc cattgctaca ggcatcgtgg tgtcacgctc gtcgtttggt atggcttcat    4380
tcagctccgg ttcccaacga tcaaggcgag ttacatgatc ccccatgttg tgcaaaaaag    4440
cggttagctc cttcggtcct ccgatcgttg tcagaagtaa gttggccgca gtgttatcac    4500
tcatggttat ggcagcactg cataattctc ttactgtcat gccatccgta agatgctttt    4560
ctgtgactgg tgagtactca accaagtcat tctgagaata gtgtatgcgg cgaccgagtt    4620
gctcttgccc ggcgtcaata cgggataata ccgcgccaca tagcagaact ttaaaagtgc    4680
tcatcattgg aaaacgttct cgggcgaa aactctcaag gatcttaccg ctgttgagat    4740
ccagttcgat gtaacccact cgtgcaccca actgatcttc agcatctttt actttcacca    4800
gcgtttctgg gtgagcaaaa acaggaaggc aaaatgccgc aaaaaaggga ataagggcga    4860
cacggaaatg ttgaatactc atactcttcc ttttcaata ttattgaagc atttatcagg    4920
gttattgtct catgagcgga tacatatttg aatgtatttta gaaaaataaa caataggggg    4980
ttccgcgcac atttccccga aaagtgccac ctgacgtcta agaaaccatt attatcatga    5040
cattaaccta taaaaatagg cgtatcacga ggccctttcg tc                       5082
```

```
<210> SEQ ID NO 4
<211> LENGTH: 15044
<212> TYPE: DNA
<213> ORGANISM: Geobacillus thermoglucosidasius

<400> SEQUENCE: 4
```

| | | | | |
|---|---|---|---|---|
| aaaatcaatc | tcttttttcca | agtttgttt | tttaaattta | gctgtctcaa | tatgtttacg | 60 |
| gtcagagcca | cgttcaccac | gcttcaactc | aaaaccctgt | ttttagttag | agaaaaaggt | 120 |
| ttcaaacaaa | aaatttaaat | cgacagagtt | atacaaatgc | cagtctcggt | gcaagtggtg | 180 |
| cgaagttgag | ttttgggaca | ttttcatat | gctcggggaa | tttatcttgt | agccataaca | 240 |
| gttcttgacg | attaaacaca | ttttttcctt | gcagttttcc | atcacgcata | ggcacaacac | 300 |
| aaaaagtata | cgagcccctt | aaatagaaca | tcggtattgt | caagaactgc | taatttgtgt | 360 |
| aaaaaaggaa | cgtcaaaagg | tagtgcgtat | ccgtgttgtg | ctaaatgcat | gtgaggggtt | 420 |
| tgctcatcat | tatgaactgt | tgcataagca | atattttgct | tgccatatcg | ttcggaaaat | 480 |
| aatttataac | tttcctcaaa | gatttacgta | cactccccaa | acgagtagta | atacttgaca | 540 |
| acgtattcgt | tataaaacga | acggtatagc | aagcctttta | ttaaatattg | aaaggagttt | 600 |
| aaatcgtttt | tgttctcctg | gatccagttg | ctcaaaaaaa | tctcggtcag | atgttactag | 660 |
| caactcattt | acaagaacag | catctttcct | cgttttttctt | tttagcaaaa | acaagaggac | 720 |
| ctaggtcaac | gagttttttt | agagccagtc | tacaatgatc | gttgagtaaa | tgttcttgtc | 780 |
| gtagaaagga | gcaaaaagaa | gtacctgttt | tttgtgattc | aataatttct | ttgacacgtt | 840 |
| cgttgtaatc | aatattttta | tcattttcta | aatcataatt | ttcacgtgtt | cgctcatggt | 900 |
| catggacaaa | aaacactaag | ttattaaaga | aactgtgcaa | gcaacattag | ttataaaaat | 960 |
| agtaaaaagt | ttagtattaa | aagtgcacaa | gcgagtacca | caatatcatc | attcgttcta | 1020 |
| cttttttcgct | ctcttgatt | atgaaattgc | atgccttta | gtccagctga | tttcactttt | 1080 |
| tgcattctac | aaactgcata | gttatagtag | taagcaagat | gaaaaagcga | gagaaactaa | 1140 |
| tactttaacg | tacggaaaat | caggtcgact | aaagtgaaaa | acgtaagatg | tttgacgtat | 1200 |
| actcatatgt | aaatcgctcc | tttttaggtg | gcacaaatgt | gaggcatttt | cgctctttcc | 1260 |
| ggcaaccact | tccaagtaaa | gtataacaca | ctatacttta | tgagtataca | tttagcgagg | 1320 |
| aaaaatccac | cgtgtttaca | ctccgtaaaa | gcgagaaagg | ccgttggtga | aggttcattt | 1380 |
| catattgtgt | gatatgaaat | tattcataaa | gtgtgtgctc | tgcgaggctg | tcggcagtgc | 1440 |
| cgaccaaaac | cataaaaacct | ttaagaccctt | tctttttttt | acgagaaaaa | agaaacaaaa | 1500 |
| ataagtattt | cacacacgag | acgctccgac | agccgtcacg | gctggttttg | gtattttgga | 1560 |
| aattctggaa | agaaaaaaaa | tgctcttttt | tcttgttttt | aaacctgccc | tctgccacct | 1620 |
| cagcaaaggg | gggttttgct | ctcgtgctcg | tttaaaaatc | agcaagggac | aggtagtatt | 1680 |
| ttttgagaag | atcactcaaa | tttgacgggg | agacggtgga | gtcgtttccc | cccaaaacga | 1740 |
| gagcacgagc | aaattttttag | tcgttccctg | tccatcataa | aaaactcttc | tagtgagttt | 1800 |
| aaatctccac | ctttaaaccc | ttgccaattt | ttattttgtc | cgtttttgtct | agcttaccga | 1860 |
| aagccagact | cagcaagaat | aaaatttta | ttgtctttcg | tttagaggtg | gaaatttggg | 1920 |
| aacggttaaa | aataaaacag | gcaaaacaga | tcgaatggct | ttcggtctga | gtcgttctta | 1980 |
| ttttaaaaat | aacagaaagc | gttttctagt | gtaacggaca | aaaccactca | aaataaaaaa | 2040 |
| gatacaagag | aggtctctcg | tatctttat | tcagcaatcg | cgcccgattg | ctgaacagat | 2100 |
| caaaagatca | cattgcctgt | tttggtgagt | tttattttt | ctatgttctc | tccagagagc | 2160 |
| atagaaaata | agtcgttagc | gcgggctaac | gacttgtcta | aataatagaa | ttttagcttt | 2220 |

```
ttatttgttg aaaaaagcta atcaaattgt tgtcgggatc aattactgca aagtctcgtt    2280
catcccacca ctgatctttt attattatct aaaatcgaaa aataaacaac tttttcgat     2340 tagtttaaca acagccctag ttaatgacgt tcagagcaa gtagggtggt gactagaaaa     2400
aatgatgtat tggggtgcaa aatgcccaaa ggcttaatat gttgatataa ttcatcaatt    2460
ccctctactt caatgcggca actagcagta ccagcaataa ttactacata accccacgtt    2520
ttacgggttt ccgaattata caactatatt aagtagttaa gggagatgaa gttacgccgt    2580
tgatcgtcat ggtcgttatt acgactccgc acctgtacaa accggtgaat cattactacg    2640
agagcgccag ccttcatcac ttgcctccca tagatgaatc cgaacctcat tacacattag   2700
tgctgaggcg tggacatgtt tggccactta gtaatgatgc tctcgcggtc ggaagtagtg    2760
aacggagggt atctacttag gcttggagta atgtgtaatc aactgcgaat ccatcttcat    2820
ggtgaaccaa agtgaaacct agtttatcgc aataaaaacc tatactcttt ttaatatccc    2880
cgactggcaa tgccgggata ttgacgctta ggtagaagta ccacttggtt tcactttgga    2940
tcaaatagcg ttattttttgg atatgagaaa aattataggg gctgaccgtt acggccctat   3000
gactgtaaca ttctcacgca taaaatcccc tttcattttc taatgtaaat ctattacctt    3060
attattaatt caattcgctc ataattaatc cttttctta ctgacattgt aagagtgcgt     3120
attttagggg aaagtaaaag attacattta gataatggaa tataattaa gttaagcgag     3180 tattaattag gaaaagaat ttacgcaaaa tggcccgatt taagcacacc ctttattccg     3240
ttaatgcgcc atgacagcca tgataattac taatactagg agaagttaat aaatacgtaa    3300
aatgcgtttt accgggctaa attcgtgtgg gaaataaggc aattacgcgg tactgtcggt    3360
actattaatg attatgatcc tcttcaatta tttatgcatt ccaacatgat taacaattat    3420
tagaggtcat cgttcaaaat ggtatgcgtt ttgacacatc cactatatat ccgtgtcgtt    3480
ctgtccactc ctgaatccca ggttgtacta attgttaata atctccagta gcaagttta    3540 ccatacgcaa aactgtgtag gtgatatata ggcacagcaa gacaggtgag gacttagggt    3600
ttccagaaat tctctagcga ttccagaagt ttctcagagt cggaaagttg accagacatt    3660
acgaactggc acagatggtc ataacctgaa ggaagatctg aaggtcttta agagatcgct    3720
aaggtcttca aagagtctca gcctttcaac tggtctgtaa tgcttgaccg tgtctaccag    3780
tattggactt ccttctagac attgcttaac tgcttcagtt aagaccgaag cgctcgtcgt    3840
ataacagatg cgatgatgca gaccaatcaa catggcacct gccattgcta cctgtacagt    3900
taacgaattg acgaagtcaa ttctggcttc gcgagcagca tattgtctac gctactacgt    3960
ctggttagtt gtaccgtgga cggtaacgat ggacatgtca caaggatggt agaaatgttg    4020
tcggtccttg cacacgaata ttacgccatt tgcctgcata ttcaaacagc tcttctacga    4080
taagggcaca aatcgcatcg gttcctacca tctttacaac agccaggaac gtgtgcttat    4140
aatgcggtaa acgacgtat aagtttgtcg agaagatgct attcccgtgt ttagcgtagc     4200
tggaacgttt gggcttctac cgatttagca gtttgataca cttttctcta agtatccacct    4260 gaatcataaa tcggcaaaat agagaaaaat tgaccatgtg accttgcaaa cccgaagatg    4320
gctaaatcgt caaactatgt gaaagagatt cataggtgga cttagtattt agccgtttta    4380
tctcttttta actggtacac taagcggcca atctgattcc acctgagatg cataatctag    4440
tagaatctct tcgctatcaa aattcacttc caccttccac tcaccggttg tccattcatg    4500
tagaatctct tcgctatcaa aattcacttc caccttccac tcaccggttg tccattcatg    4500
attcgccggt tagactaagg tggactctac gtattagatc atcttagaga agcgatagtt    4560
ttaagtgaag gtggaaggtg agtggccaac aggtaagtac gctgaactct gcttcctctg    4620
```

```
ttgacatgac acacatcatc tcaatatccg aataggcccc atcagtctga cgaccaagag    4680
agccataaac accaatagcc cgacttgaga cgaaggagac aactgtactg tgtgtagtag    4740
agttataggc ttatcccggg tagtcagact gctggttctc tcggtatttg tggttatcgg    4800
ttaacatcat ccccatattt atccaatatt cgttccttaa tttcatgaac aatcttcatt    4860 cttcttctc tagtcattat tattggtcca ttcactattc aattgtagta ggggtataaa    4920
taggttataa gcaaggaatt aaagtacttg ttagaagtaa gaaagaagag atcagtaata    4980
ataaccaggt aagtgataag tcattcccct ttcagataat tttagatttg cttttctaaa    5040
taagaatatt tggagagcac cgttcttatt cagctattaa taactcgtct tcctaagcat    5100
agtaagggaa aagtctatta aaatctaaac gaaaagattt attcttataa acctctcgtg    5160
gcaagaataa gtcgataatt attgagcaga aggattcgta ccttcaatcc ttttaataac    5220
aattatagca tctaatcttc aacaaactgg cccgtttgtt gaactactct ttaataaaat    5280 aattttccg ttcccaattc ggaagttagg aaaattattg ttaatatcgt agattagaag    5340
ttgtttgacc gggcaaacaa cttgatgaga aattatttta ttaaaaaggc aagggttaag    5400
cacattgcaa taatagaaaa tccatcttca tcggcttttt cgtcatcatc tgtatgaatc    5460
aaatcgcctt cttctgtgtc atcaaggttt aattttttat gtgtaacgtt attatctttt    5520
aggtagaagt agccgaaaaa gcagtagtag acatacttag tttagcggaa gaagacacag    5580
tagttccaaa ttaaaaaata gtatttcttt taacaaacca ccataggaga ttaacctttt    5640
acggtgtaaa ccttcctcca aatcagacaa acgtttcaaa ttcttttctt catcatcggt    5700
cataaagaaa attgtttggt ggtatcctct aattggaaaa tgccacattt ggaaggaggt    5760
ttagtctgtt tgcaaagttt aagaaaagaa gtagtagcca cataaaatcc gtatccttta    5820
caggatattt tgcagtttcg tcaattgccg attgtatatc cgatttatat ttattttcg    5880 gtcgaatcat ttgaactttt gtattttagg cataggaaat gtcctataaa acgtcaaagc    5940
agttaacggc taacatatag gctaaatata aataaaaagc cagcttagta aacttgaaaa    6000
acatttggat catagtctaa tttcattgcc tttttccaaa attgaatcca ttgttttga    6060 ttcacgtagt tttctgtatt cttaaaataa gttggttcca tgtaaaccta gtatcagatt    6120
aaagtaacgg aaaaaggttt taacttaggt aacaaaaact aagtgcatca aaagacataa    6180
gaattttatt caaccaaggt cacataccaa tacatgcatg tgctgattat aagaattatc    6240
tttattattt attgtcactt ccgttgcacg cataaaacca acaagatttt tattaattt    6300 gtgtatggtt atgtacgtac acgactaata ttcttaatag aaataataaa taacagtgaa    6360
ggcaacgtgc gtattttggt tgttctaaaa ataattaaaa tttatattgc atcattcggc    6420
gaaatccttg agccatatct gacaaactct tatttaattc ttcgccatca taaacatttt    6480
taactgttaa tgtgagaaac aaatataacg tagtaagccg ctttaggaac tcggtataga    6540
ctgtttgaga ataaattaag aagcggtagt atttgtaaaa attgacaatt acactctttg    6600
aaccaacgaa ctgttggctt tgttttaata acttcagcaa caaccttttg tgactgaatg    6660
ccatgtttca ttgctctcct ccagttgcac attggacaaa ttggttgctt gacaaccgaa    6720
aacaaattat tgaagtcgtt gttggaaaac actgacttac ggtacaaagt aacgagagga    6780
ggtcaacgtg taacctgttt gcctggattt acaaaaccac actcgataca actttctttc    6840
gcctgtttca cgattttgtt tatactctaa tatttcagca caatcttta ctctttcagc    6900 cggacctaaa tgttttggtg tgagctatgt tgaaagaaag cggacaaagt gctaaaacaa    6960
atatgagatt ataaagtcgt gttagaaaat gagaaagtcg cttttttaaat tcaagaatat    7020
```

```
gcagaagttc aaagtaatca acattagcga ttttcttttc tctccatggt ctcactttc    7080 cactttttgt cttgtccact gaaaaattta agttcttata cgtcttcaag tttcattagt   7140
tgtaatcgct aaaagaaaag agaggtacca gagtgaaaag gtgaaaaaca gaacaggtga   7200 aaaaccctg atttttcatc tgaataaatg ctactattag gacacataat attaaaagaa    7260 accccatct atttagttat tgtttagtc acttataact ttttgggaac taaaaagtag     7320
acttatttac gatgataatc ctgtgtatta aattttctt tgggggtaga taaatcaata    7380
aacaaatcag tgaatattga ttaacagatg ggttttttct gtgcaaccaa ttttaagggt   7440
tttcaatact ttaaaacaca tacataccaa cacttcaacg caccttttcag caactaaaat  7500 aattgtctac cccaaaaaga cacgttggtt aaaattccca aaagttatga attttgtgt    7560 atgtatggtt gtgaagttgc gtggaaagtc gttgatttta aaaaatgacg ttatttctat   7620
atgtatcaag ataagaaaga acaagttcaa aaccatcaaa aaaagacacc ttttcaggtg   7680
ctttttttat tttataaact ttttactgc aataaagata tacatagttc tattctttct    7740
tgttcaagtt ttggtagttt ttttctgtgg aaaagtccac gaaaaaaata aaatatttga   7800
cattccctga tctcgacttc gttctttttt tacctctcgg ttatgagtta gttcaaattc   7860
gttcttttta ggttctaaat cgtgttttc ttggaattgt gtaagggact agagctgaag    7920
caagaaaaaa atggagagcc aatactcaat caagttaagc caagaaaaat ccaagattta   7980
gcacaaaaag aaccttaaca gctgttttat cctttacctt gtctacaaac cccttaaaaa   8040 cgttttaaa ggcttttaag ccgtctgtac gttccttaag gaattcactg gccgtcgttt    8100
cgacaaaata ggaaatggaa cagatgtttg gggaatttt gcaaaaattt ccgaaaattc    8160
ggcagacatg caaggaattc cttaagtgac cggcagcaaa tacaacgtcg tgactgggaa   8220
aaccctggcg ttacccaact taatcgcctt gcagcacatc cccctttcgc cagctggcgt   8280
aatagcgaag aggcccgcac atgttgcagc actgacccttt tgggaccgc aatgggttga   8340 attagcggaa cgtcgtgtag gggaaagcg gtcgaccgca ttatcgcttc tccgggcgtg    8400
cgatcgccct tcccaacagt tgcgcagcct gaatggcgaa tggcgcctga tgcggtattt   8460
tctccttacg catctgtgcg gtatttcaca ccgcatatgg gctagcggga agggttgtca   8520
acgcgtcgga cttaccgctt accgcggact acgccataaa agaggaatgc gtagacacgc   8580
cataaagtgt ggcgtatacc tgcactctca gtacaatctg ctctgatgcc gcatagttaa   8640
gccagccccg acaccgcca acacccgctg acgcgccctg acgggcttgt ctgctcccgg    8700
acgtgagagt catgttagac gagactacgg cgtatcaatt cggtcggggc tgtgggcggt   8760
tgtgggcgac tgcgcgggac tgcccgaaca gacgagggcc catccgctta cagacaagct   8820
gtgaccgtct ccgggagctg catgtgtcag aggttttcac cgtcatcacc gaaacgcgcg   8880
agacgaaagg gcctcgtgat gtaggcgaat gtctgttcga cactggcaga ggccctcgac   8940
gtacacagtc tccaaaagtg gcagtagtgg ctttgcgcgc tctgctttcc cggagcacta   9000
acgcctattt ttataggtta atgtcatgat aataatggtt tcttagacgt caggtggcac   9060
ttttcgggga aatgtgcgcg gaaccccctat ttgtttattt tgcggataaa aatatccaat   9120
tacagtacta ttattaccaa agaatctgca gtccaccgtg aaaagcccct ttacacgcgc   9180
cttggggata aacaaataaa ttctaaatac attcaaatat gtatccgctc atgagacaat   9240
aaccctgata aatgcttcaa taatattgaa aaaggaagag tatgagtatt caacatttcc   9300
aagatttatg taagtttata cataggcgag tactctgtta ttgggactat ttcgaagtt    9360 attataactt tttccttctc atactcataa gttgtaaagg gtgtcgccct tattcccttt   9420
```

```
tttgcggcat tttgccttcc tgtttttgct cacccagaaa cgctggtgaa agtaaaagat    9480
gctgaagatc agttgggtgc cacagcggga ataagggaaa aaacgccgta aaacggaagg    9540
acaaaaacga gtgggtcttt gcgaccactt tcattttcta cgacttctag tcaacccacg    9600
acgagtgggt tacatcgaac tggatctcaa cagcggtaag atccttgaga gttttcgccc    9660
cgaagaacgt tttccaatga tgagcacttt taaagttctg tgctcaccca atgtagcttg    9720
acctagagtt gtcgccattc taggaactct caaaagcggg gcttcttgca aaaggttact    9780
actcgtgaaa atttcaagac ctatgtggcg cggtattatc ccgtattgac gccgggcaag    9840
agcaactcgg tcgccgcata cactattctc agaatgactt ggttgagtac tcaccagtca    9900
gatacaccgc gccataatag ggcataactg cggcccgttc tcgttgagcc agcggcgtat    9960
gtgataagag tcttactgaa ccaactcatg agtggtcagt cagaaaagca tcttacggat   10020
ggcatgacag taagagaatt atgcagtgct gccataacca tgagtgataa cactgcggcc   10080
aacttacttc tgacaacgat gtcttttcgt agaatgccta ccgtactgtc attctcttaa   10140
tacgtcacga cggtattggt actcactatt gtgacgccgg ttgaatgaag actgttgcta   10200
cggaggaccg aaggagctaa ccgcttttt gcacaacatg ggggatcatg taactcgcct   10260
tgatcgttgg gaaccggagc tgaatgaagc cataccaaac gcctcctggc ttcctcgatt   10320
ggcgaaaaaa cgtgttgtac ccctagtac attgagcgga actagcaacc cttgcctcg   10380 acttacttcg gtatggtttg gacgagcgtg acaccacgat gcctgtagca atggcaacaa   10440
cgttgcgcaa actattaact ggcgaactac ttactctagc ttcccggcaa caattaatag   10500
ctgctcgcac tgtggtgcta cggacatcgt taccgttgtt gcaacgcgtt tgataattga   10560
ccgcttgatg aatgagatcg aagggccgtt gttaattatc actggatgga ggcggataaa   10620
gttgcaggac cacttctgcg ctcggccctt ccggctggct ggtttattgc tgataaatct   10680
ggagccggtg agcgtgggtc tgacctacct ccgcctattt caacgtcctg gtgaagacgc   10740
gagccgggaa ggccgaccga ccaaataacg actatttaga cctcggccac tcgcacccag   10800
tcgcggtatc attgcagcac tggggccaga tggtaagccc tcccgtatcg tagttatcta   10860
cacgacgggg agtcaggcaa ctatggatga acgaaataga agcgccatag taacgtcgtg   10920
accccggtct accattcggg agggcatagc atcaatagat gtgctgcccc tcagtccgtt   10980 gataccactct tgctttatct cagatcgctg agataggtgc ctcactgatt aagcattggt   11040
aactgtcaga ccaagtttac tcatatatac tttagattga tttaaaactt catttttaat   11100
gtctagcgac tctatccacg gagtgactaa ttcgtaacca ttgacagtct ggttcaaatg   11160
agtatatatg aaatctaact aaattttgaa gtaaaaatta ttaaaaggat ctaggtgaag   11220 atccttttg ataatctcat gaccaaaatc ccttaacgtg agttttcgtt ccactgagcg   11280
tcagaccccg tagaaaagat aattttccta gatccacttc taggaaaaac tattagagta   11340
ctggttttag ggaattgcac tcaaaagcaa ggtgactcgc agtctggggc atcttttcta   11400
caaaggatct tcttgagatc cttttttct gcgcgtaatc tgctgcttgc aaacaaaaaa   11460
accaccgcta ccagcggtgg tttgtttgcc ggatcaagag gttcctaga agaactctag   11520 gaaaaaaga cgcgcattag acgacgaacg tttgttttt tggtggcgat ggtcgccacc   11580
aaacaaacgg cctagttctc ctaccaactc tttttccgaa ggtaactggc ttcagcagag   11640
cgcagatacc aaatactgtc cttctagtgt agccgtagtt aggccaccac ttcaagaact   11700
gatggttgag aaaaaggctt ccattgaccg aagtcgtctc gcgtctatgg tttatgacag   11760
gaagatcaca tcggcatcaa tccggtggtg aagttcttga ctgtagcacc gcctacatac   11820
```

```
ctcgctctgc taatcctgtt accagtggct gctgccagtg gcgataagtc gtgtcttacc    11880
gggttggact caagacgata gacatcgtgg cggatgtatg gagcgagacg attaggacaa    11940
tggtcaccga cgacggtcac cgctattcag cacagaatgg cccaacctga gttctgctat    12000
gttaccggat aaggcgcagc ggtcgggctg aacgggggt tcgtgcacac agcccagctt     12060
ggagcgaacg acctacaccg aactgagata cctacagcgt caatggccta ttccgcgtcg    12120
ccagcccgac ttgcccccca agcacgtgtg tcggtcgaa cctcgcttgc tggatgtggc     12180
ttgactctat ggatgtcgca gagctatgag aaagcgccac gcttcccgaa gggagaaagg    12240
cggacaggta tccggtaagc ggcagggtcg gaacaggaga gcgcacgagg gagcttccag    12300
ctcgatactc tttcgcggtg cgaagggctt ccctctttcc gcctgtccat aggccattcg    12360
ccgtcccagc cttgtcctct cgcgtgctcc ctcgaaggtc ggggaaacgc ctggtatctt    12420
tatagtcctg tcgggtttcg ccacctctga cttgagcgtc gattttgtg atgctcgtca     12480 gggggcgga gcctatggaa cccctttgcg gaccatagaa atatcaggac agcccaaagc     12540
ggtggagact gaactcgcag ctaaaaacac tacgagcagt cccccgcct cggatacctt      12600 aaacgccagc aacgcggcct ttttacggtt cctggccttt tgctggcctt ttgctcacat    12660 gttcttttcct gcgttatccc ctgattctgt ggataaccgt tttgcggtcg ttgcgccgga   12720
aaaatgccaa ggaccggaaa acgaccggaa acgagtgta caagaaagga cgcaataggg     12780
gactaagaca cctattggca attaccgcct ttgagtgagc tgataccgct cgccgcagcc    12840
gaacgaccga gcgcagcgag tcagtgagcg aggaagcgga agagcgccca atacgcaaac    12900
taatggcgga aactcactcg actatggcga gcggcgtcgg cttgctggct cgcgtcgctc    12960
agtcactcgc tccttcgcct tctcgcgggt tatgcgtttg cgcctctccc cgcgcgttgg    13020
ccgattcatt aatgcagctg gcacgacagg tttcccgact ggaaagcggg cagtgagcgc    13080
aacgcaatta atgtgagtta gcggagaggg gcgcgcaacc ggctaagtaa ttacgtcgac    13140
cgtgctgtcc aaagggctga ccttctcgccc gtcactcgcg ttgcgttaat tacactcaat   13200
gctcactcat taggcacccc aggctttaca ctttatgctt ccggctcgta tgttgtgtgg    13260
aattgtgagc ggataacaat ttcacacagg aaacagctat cgagtgagta atccgtgggg    13320
tccgaaatgt gaaatacgaa ggccgagcat acaacacacc ttaacactcg cctattgtta    13380
aagtgtgtcc tttgtcgata gaccatgatt acgccaagct tgcatgcctg caggtcgact    13440
cccttatgaa ccaaggaata gcagatgagt tagtattgat tgatgtaaat aagaataagg    13500
ctggtactaa tgcggttcga acgtacggac gtccagctga gggaatactt ggttccttat    13560
cgtctactca atcataacta actacatta ttcttattcc cagagggcga tgtgatggat     13620
ttaaatcacg gaaagtatt cgcgccgaag ccgatgaata tttggtttgg agattatcaa     13680
gattgccaag acgccgattt gtctcccgct acactaccta aatttagtgc cttttcataa    13740
gcgcggcttc ggctacttat aaaccaaacc tctaatagtt ctaacggttc tgcggctaaa    13800
ggtggtgatt tgtgcagggg ctaaccaaaa gccgggagaa acaagactgg atcttgttga    13860 caaaatatt aatatcttca aaacgattgt cgattctgtg ccaccactaa acacgtcccc      13920
gattggtttt cggcccctctt tgttctgacc tagaacaact gttttataa ttatagaagt     13980 tttgctaaca gctaagacac atgaaatccg gatttgatgg cgttttctt gtggcaacga     14040 acccagtgga tattttaacg tatgctactt ggaaatttag cgggttaccg aaagagcggg    14100
tactttaggc ctaaactacc gcaaaaagaa caccgttgct tgggtcacct ataaaattgc    14160
atacgatgaa cctttaaatc gcccaatggc tttctcgccc tgcggccgcc ttgctaagtg    14220
```

```
aatattttca agtggctccg accaatgtac atgcgtatat tattggcgag catggggata    14280
cagagctgcc tgtttggagc acgccggcgg aacgattcac ttataaaagt tcaccgaggc    14340
tggttacatg tacgcatata ataaccgctc gtacccctat gtctcgacgg acaaacctcg    14400
catgcggaaa ttggaagcat tccagttgag caaatattga tgcaaaacga taactataga    14460
aaagaggatt tagacaatat ctttgttaat gttcgtgatg gtacgccttt aaccttcgta    14520
aggtcaactc gtttataact acgttttgct attgatatct tttctcctaa atctgttata    14580
gaaacaatta caagcactac cggcatatca aatcattgag aaaaaagggg caacgtatta    14640
cggcattgca atgggattag tccgtatcac tcgtgctatt ttgcacaatg aaaatgccat    14700
gccgtatagt ttagtaactc tttttccc gttgcataat gccgtaacgt taccctaatc      14760
aggcatagtg agcacgataa aacgtgttac ttttacggta cttaaccgtt tctgctcatt    14820
tggacggcca atatggcgaa cgaaatgttt atattggcgt gcctgccatt atcaaccgaa    14880
acggtattcg tgaagtgatg gaattggcaa agacgagtaa acctgccggt tataccgctt    14940
gctttacaaa tataaccgca cggacggtaa tagttggctt tgccataagc acttcactac    15000
gaattgacgc tgcaggcatg cacttaactg cgacgtccgt acgt                     15044
```

SPORULATION-DEFICIENT THERMOPHILIC MICROORGANISMS FOR THE PRODUCTION OF ETHANOL

CROSS-REFERENCE TO RELATED APPLICATION

This application is the U.S. national stage application of International Patent Application No. PCT/GB2009/051487, filed Nov. 5, 2009, the disclosure of which is hereby incorporated by reference in its entirety, including all figures, tables and amino acid or nucleic acid sequences.

FIELD OF THE INVENTION

This invention relates to the production of microorganisms suitable for the production of ethanol. In particular, the invention relates to the modification of microorganisms to prevent sporulation.

BACKGROUND TO THE INVENTION

Sporulation is a multi-stage developmental process that is responsible for the conversion of a growing cell into a dormant cell type, known as a spore or endospore. Spores are adapted for dispersal and survival for an extended period of time in unfavourable conditions and form part of the life cycle of many plants, algae and bacteria, such as the *Bacillus* species.

The primary regulator for entry into sporulation is the DNA-binding protein Spo0A (stage 0 sporulation protein A), which is a member of the response regulator family of transcription factors. Numerous other genes, including genes which encode five histidine autokinases (KinA, KinB, KinC, KinD and KinE) and two response proteins (Spo0B and Spo0F), are also involved in the control of the initiation of sporulation (Molle et al.; Mol. Microbial.; 2003, 50(5):1683-1701). The activity of Spo0A is governed by a multi-component phosphorelay, which recognises and integrates environmental signals to initiate sporulation (Trach K A, et al; Mol. Microbiol. 1993; 8(1):69-79). Upon phosphorylation of its regulatory N-terminal domain, Spo0A-P binds to a DNA sequence element known as the "0A-box" which activates genes involved in sporulation. Deletion of the C-terminal domain of Spo0A, which is inactive until the N-terminus has been phosphorylated, has been shown to result in a sporulation-negative phenotype (Rowe-Magnus DA, et al; J. Bacteriol.; 2000; 182(15):4352-4355).

Spo0A has also been found to influence, directly or indirectly, the activation or repression of expression of over 500 genes in *B. subtilis*, and therefore indirectly mediates the global pattern of gene transcription via regulatory genes under its control (Molle et al.; Mol. Microbiol.; 2003, 50(5): 1683-1701).

Sporulation is subject to catabolite repression, whereby the presence of glucose or other readily metabolized carbon sources inhibits sporulation by wild-type cells. In particular, glucose is known to repress the transcription of spo0A and spo0F (Myseliwiec, TH et al; J. Bacterial.; 1991; 173(6): 1911-1919). In a commercial fermentation process spores are undesirable for two main reasons:
1. Sporulation pauses active metabolism by an organism resulting in a reduction or cessation of the formation of a desired metabolic product; and
2. Sporulating microorganisms are more difficult to handle and control containment, therefore it is desirable to avoid the survival of commercial process microorganisms for environmental reasons, including health and safety, and also to prevent the uncontrolled release of the commercial strain.

The general process by which bacteria metabolise suitable substrates is glycolysis, which is a sequence of reactions that converts glucose into pyruvate with the generation of ATP. The fate of pyruvate in the generation of metabolic energy varies depending on the microorganism and the environmental conditions. The four principal reactions of pyruvate are illustrated in FIG. 5.

First, under aerobic conditions, many microorganisms will generate energy using the citric acid cycle and the conversion of pyruvate into acetyl coenzyme A, catalysed by pyruvate dehydrogenase (PDH).

Second, under anaerobic conditions, certain ethanologenic organisms can carry out alcoholic fermentation by the decarboxylation of pyruvate into acetaldehyde, catalysed by pyruvate decarboxylase (PDC) and the subsequent reduction of acetaldehyde into ethanol by NADH, catalysed by alcohol dehydrogenase (ADH).

A third reaction, which also occurs in anaerobic conditions, is the conversion of pyruvate to acetyl CoA, catalysed by pyruvate formate lyase (PFL). Acetyl CoA is subsequently converted into acetaldehyde by the enzyme acetaldehyde dehydrogenase (AcDH) and ethanol is produced by the reduction of acetaldehyde catalysed by ADH.

A fourth process is the conversion of pyruvate into lactate which occurs through catalysis by lactate dehydrogenase (LDH).

There has been much interest in using microorganisms for the production of ethanol using either microorganisms that undergo anaerobic fermentation naturally or through the use of recombinant microorganisms which incorporate the pyruvate decarboxylase and alcohol dehydrogenase genes.

WO2008/038019 discloses microorganisms which comprise modifications to inactivate the native LDH and PFL genes and up-regulate the PDC, PDH and ADH genes in order to promote the formation of ethanol.

There is a need for further improvements to the production of ethanol from microorganisms.

SUMMARY OF THE INVENTION

The present invention is based upon the surprising finding that inhibition of the spo0A gene in spore-forming thermophilic microorganisms results in increased ethanol tolerance of the microorganism, and also increased metabolism, which results in an increase in the rate of production of metabolic end-products such as ethanol.

According to a first aspect of the present invention, a thermophilic microorganism comprises a modification that decreases sporulation compared with wild-type, wherein a first modification inactivates the native spo0A gene.

The microorganism may be further modified to permit increased production of ethanol via inactivation of the native lactate dehydrogenase and, optionally, pyruvate formate lyase genes. Further modification can be made to upregulate the native pyruvate dehydrogenase gene or introducing an active pyruvate decarboxylase gene.

The microorganism may be further modified to permit increased production of ethanol from starch by increasing amylase gene expression.

The microorganism of the invention shows increased ethanol production and increased ethanol tolerance compared to wild-type.

According to a second aspect of the present invention, a method of producing ethanol comprises culturing a microorganism according to the definition provided above in suitable conditions in the presence of a C3, C5 or C6 sugar, or an oligomer thereof.

DESCRIPTION OF THE DRAWINGS

The present invention is described with reference to the accompanying figures, wherein:

FIG. 1 is the Spo0A nucleotide sequence (SEQ ID No. 1);
FIG. 2 is the Spo0A amino acid sequence (SEQ ID No. 2)

DETAILED DESCRIPTION OF THE INVENTION

Figure 3:
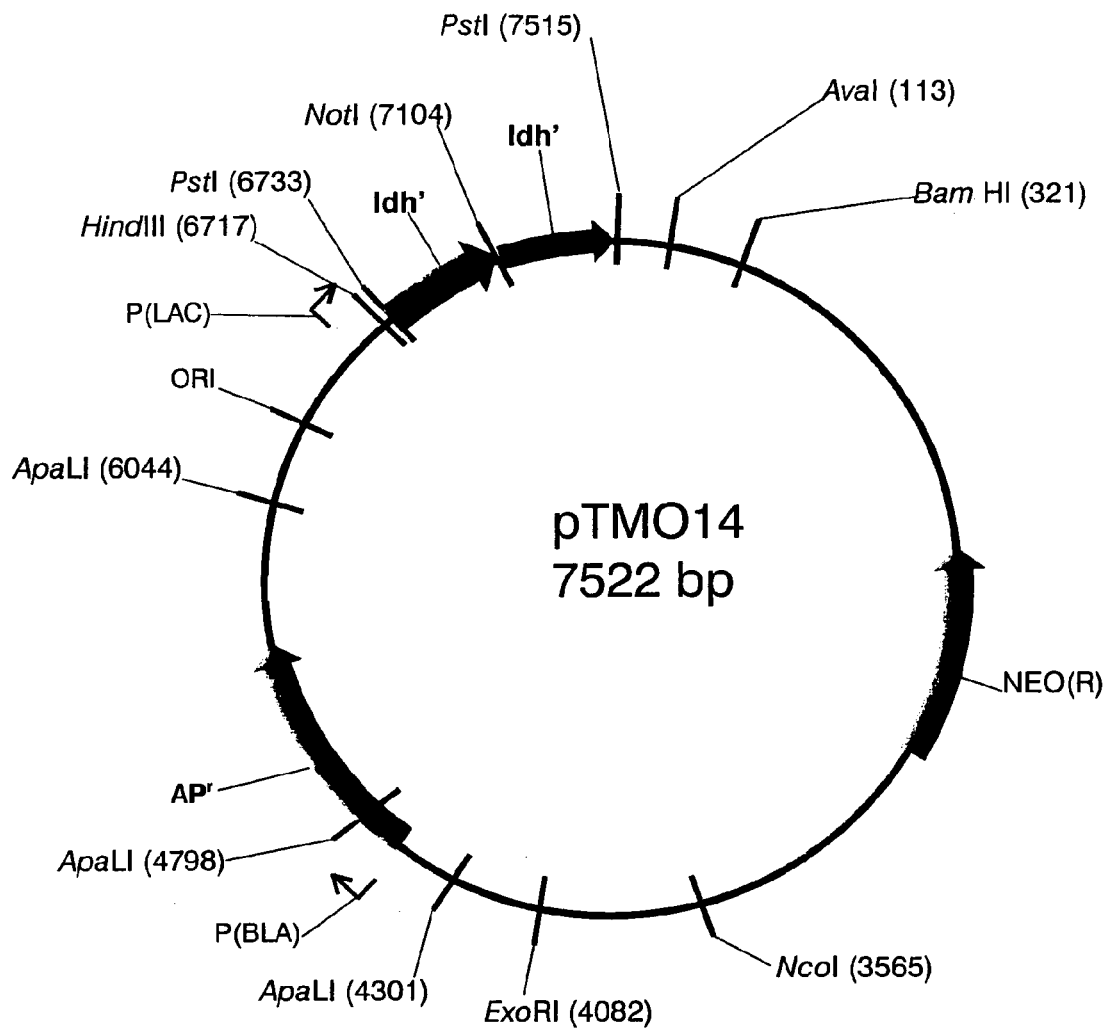
FIG. 3 illustrates the plasmid pTM014 (SEQ ID No. 4)

The present invention relates to the modification of a thermophilic microorganism to prevent sporulation.

The invention is based upon the surprising finding that inhibition of sporulation is associated with increased ethanol tolerance, enabling larger yields of ethanol to be produced by microorganisms in batch fermentation processes. Non-sporulating microorganisms also have process advantages since they are easier to handle and control than spore-formers.

Furthermore, due to an increase in metabolism, it has been found that fermentation proceeds to completion at a faster rate when sporulation is prevented.

Sporulation can be prevented by modifying the microorganism to inactivate the native spo0A gene, preferably by deleting at least a portion of the spo0A gene or by targeted disruption of the gene. Preferably, as a result of the modification the microorganism is entirely sporulation-deficient.

The coding sequence of the spo0A gene (SEQ ID No. 1) is shown in FIG. 1. The amino acid sequence of the polypeptide encoded by the spo0A gene (SEQ ID No. 2) is shown in FIG. 2. Using this coding sequence, it is possible for the skilled person to target spo0A to achieve inactivation of the gene through different mechanisms. It is preferred if the spo0A gene is inactivated by the deletion of the gene sequence, or a portion thereof, preferably the C-terminal domain.

Methods to inactivate the gene will be apparent to the skilled person, based on the knowledge of the gene sequence, as disclosed herein The gene sequence may be deleted or inactivated by insertion of additional DNA to the disrupt gene expression.

Methods of targeted gene disruption are well known in the art and include, for example, the integration of temperature-sensitive plasmids into the target gene on the chromosome. Integration of a plasmid may delete the target gene entirely, or may replace the complete gene with a portion of the gene that is non-functional. This can be achieved by isolating a sequence that includes the gene of interest, excising a portion of the gene, amplifying the remaining fragments, cloning these fragments into a temperature-sensitive plasmid and then transforming target microorganisms with the plasmid. The present invention is not limited to a specific method of inactivating the spo0A gene, however a detailed description of a suitable technique using the plasmid pTMO31 is provided in the 'Example' section.

The microorganism may be any thermophilic microorganism, but it is preferred if the microorganism is of the *Bacillus* species. In particular, it is preferred if the microorganism is a wild-type microorganism of the *Geobacillus* species, in particular *Geobacillus thermoglucosidasius*.

In a preferred embodiment, the microorganisms selected for modification are said to be "wild-type", i.e. they do not comprise any further laboratory-produced mutations in addition to the mutations described herein. The microorganisms may be isolated from environmental samples expected to contain thermophiles. Isolated wild-type microorganisms will have the ability to sporulate. Furthermore, isolated wild-type microorganisms will have the ability to produce ethanol from pyruvate but, unmodified, lactate is likely to be the major fermentation product. The isolates are selected for their ability to grow on hexose and/or pentose sugars, and oligomers thereof, at thermophilic temperatures.

It is preferable that the microorganism of the invention has certain desirable characteristics which permit the microorganism to be used in a fermentation process. The microorganism should preferably have no restriction system, thereby avoiding the need for in vivo methylation. In addition, the microorganism should be stable to at least 3% w/v ethanol, preferably 5-10% w/v ethanol, and most preferably up to 20% w/v ethanol. The microorganisms should have the ability to utilise $C_3$, $C_5$ and $C_6$ sugars (or their oligomers) as a substrate, including cellulose, cellobiose, hemicellulose, starch and xylan. It is preferable if the microorganism is transformable at a high frequency. Furthermore, the microorganism should have a growth rate in continuous culture to support dilution rates of 0.3 $h^{-1}$ and above.

The microorganism will be a thermophile and will grow in the temperature range of 40° C.-85° C. Preferably, the microorganism will grow within the temperature range 50° C.-70° C. In addition, it is desirable that the microorganism grows in conditions of pH 8 or below, in particular pH 4.5-pH 6.9.

Preferred microorganisms of the invention are identified herein as TM443 and TM444, each of which have been accepted for deposit at NCIMB Ltd., Ferguson Building, Craibstone Estate, Bucksburn, Aberdeen AB21 9YA, on 31 Oct. 2008 (Accession Nos. 41591 and 41588, respectively).

The thermophilic microorganism of the invention may be further modified to disrupt the expression of the lactate dehydrogenase gene (LDH).

Inactivating the lactate dehydrogenase gene helps to prevent the breakdown of pyruvate into lactate, and therefore promotes (under appropriate conditions) the breakdown of pyruvate into ethanol using pyruvate decarboxylase and alcohol dehydrogenase. It is preferable for the lactate dehydrogenase gene to be disrupted by a deletion within, or of, the gene.

The nucleic acid sequence for lactate dehydrogenase is now known. Using this sequence, it is possible for the skilled person to target the lactate dehydrogenase gene to achieve inactivation of the gene through different mechanisms. It is possible to inactivate the lactate dehydrogenase gene by the insertion of a transposon. However, it is preferred if the lactate dehydrogenase gene is inactivated by the deletion of the gene sequence or a portion of the gene sequence. Deletion is preferred, as this avoids the difficulty of reactivation of the gene sequence which is often experienced when transposon inactivation is used. In a preferred embodiment, the lactate dehydrogenase gene is inactivated by the integration of a temperature-sensitive plasmid, which achieves natural homologous recombination or integration between the plasmid and the microorganism's chromosome. Preferably, the plasmid is pTM014 (SEQ ID No. 4), which is illustrated in FIG. 3. Chromosomal integrants can be selected for on the basis of their resistance to antibacterial agents. The integration into the lactate dehydrogenase gene may occur by a single cross-over recombination event or by a double (or more) cross-over recombination event.

The microorganism may also be modified to up-regulate the pyruvate dehydrogenase gene (PDH). Up-regulating the pyruvate dehydrogenase gene promotes the conversion of pyruvate into acetyl CoA, which can then be used, under appropriate conditions, to produce acetaldehyde and eventually ethanol using acetaldehyde dehydrogenase. A further advantage of up-regulating PDH is that pyruvate levels, which have an inhibitory effect on glucose uptake and glycolysis, are reduced. This further promotes ethanol production. PDH is a large enzyme complex, containing three units—E1: pyruvate decarboxylase (EC 1.2.4.1, not EC 4.1.1.1), E2: dihydrolipoamide transacetylase, and E3: dihydrolipoamide dehydrogenase. The complex requires several cofactors, including NAD, FAD, coenzyme A lipoic acid and thiamine pyrophosphate (TPP). Four genes code for the complex, as the E1 unit is a heterodimer of α and β subunits, and are often described as pdhA, pdhB, pdhC and pdhD (E1α, E1, E2β and E3 respectively). The E1 unit of PDH requires TPP in the same way that PDC (EC 4.1.1.1) requires TPP and catalyses a similar decarboxylation reaction, but in the presence of coenzyme A and lipoic acid—carried by other enzyme units—the product is acetyl CoA rather than acetaldehyde. However, PDC activity of the E1 unit has been measured when it has not been complexed with other units in PDH (Lessard & Perham; *The Journal of Biological Chemistry*; 1994, 269; 14, 10378-10383; Tomar et al; *Applied Microbiology and Biotechnology*; 2003, 62, 76-82; Frank et al; *Science*; 2004, 306; October 29, 872-876, supplementary data). Accordingly, PDC activity of EC 1.2.4.1 may be enhanced by the up-regulation of PDH so that acetaldehyde is produced over and above acetyl CoA. Enhanced PDH activity is also sought to remove the pyruvate bottleneck observed in LDH inactivated strains to allow more ethanol to be produced with less acetate and formate as side products.

To this end, the PDH genes and surrounding sequence were isolated using standard "genome walking" techniques. Approximately 8.8 kb of DNA was isolated, sequenced and found to contain the following genes shown in FIG. 4 and Table 1.

TABLE 1

| Gene | Position (bp) | Proposed Function | Frame (aa's at 5' and 3') | Size (aa) |
| --- | --- | --- | --- | --- |
| pdf2 | 746-192 | Peptide deformylase | −3 (MIT-IER) | 184 |
| orf2 | 868-1497 | Unknown - Hypothetical protein | +1 (MQR-IWK) | 209 |
| pdhA(α) | 1875-2984 | α-subunit of pyruvate hydrogenase | +3 (MGA-ESK) | 369 |
| pdhA(β) | 3003-3965 | β-subunit of pyruvate dehydrogenase | +3 (MIQ-INF) | 320 |

TABLE 1-continued

| Gene | Position (bp) | Proposed Function | Frame (aa's at 5' and 3') | Size (aa) |
| --- | --- | --- | --- | --- |
| pdhB | 4058-5368 | Dihydrolipoamide transacetylase | +2 (VAF-MEA) | 436 |
| lpd | 5373-6785 | Lipoamide dehydrogenase | +3 (MVV-ISK) | 470 |
| orf7 | 7432-6833 | Unknown - Hypothetical protein | −1 (MNK-CTE) | 199 |
| orf8 | 7964-8647 | Transposase | +2 (MDL-SPP) | 227 |

Figure 4:
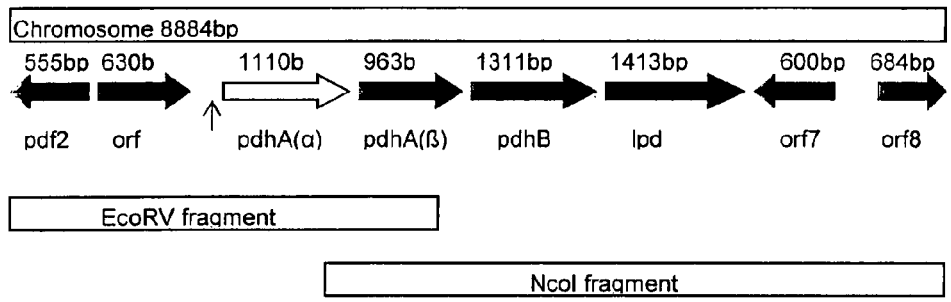
FIG. 4 illustrates the hypothetical promoter regions and genes of the PDH complex.
Figure 5:
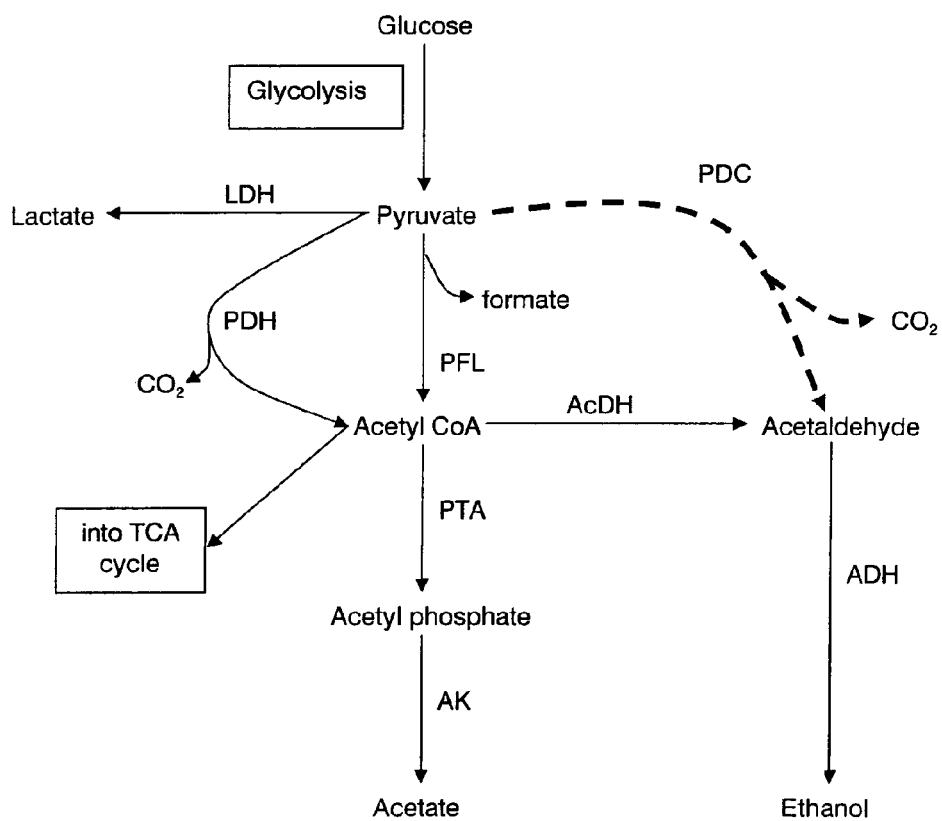
FIG. 5 illustrates the four principal reactions of pyruvate.

The hypothetical promoter regions are shown in FIG. 4 (arrow)—one upstream from the start of pdhA and a possible second promoter ahead of pdhB. A previous example of a secondary promoter in the PDH cluster was reported for *Bacillus subtilis* (Gao et al; *Journal of Bacteriology*, 2002, 184:10, 2780-2788), but most described PDH gene clusters have just one promoter upstream of the cluster (Neveling et al; *Biochimica Acta*; 1998 1385. 367-372). The upregulation can be carried out using techniques known in the art. In particular, upregulation can be carried out by introducing a suitable promoter or enhancer sequence upstream of the PDH complex.

The enzyme complex is known to work under both aerobic and anaerobic conditions (Carlsson et al; *Infection and Immunity*; 1985, 49(3):674-678) but it is generally considered to be an aerobic enzyme (Ch 15; Principles of Biochemistry; Lehninger, Nelson & Cox; 2$^{nd}$ Ed, Worth Publishers, New York, 1993, p 447) with pyruvate formate lyase (PFL) its anaerobic counterpart. Both enzymes convert pyruvate, formed in glycolysis, to acetyl CoA to feed into the TCA cycle but the cycle only works completely under aerobic conditions. However, as it is desirable to use anaerobic conditions, promoters that operate in anaerobic conditions are preferred for use in the invention. Thus promoters for enzymes believed to work under anaerobic conditions—examples being the LDH promoter (P_ldh from *G. stearothermophilus* NCA1503), the PFL promoters (P_pfl from *B. cereus* ATCC14579, and *G. thermoglucosidasius* NCIMB11955) and ferredoxin promoters (P_ferrA from *G. stearothermophilus* DSM13240)—can be used, as in PCT/GB2007/03699 which is incorporated herein by reference.

In a preferred embodiment, a further modification is introduced to enhance the PDC activity, thereby promoting the conversion of pyruvate to acetaldehyde. This can be carried out by inactivating E2 (EC 2.3.1.12). Inactivation can be carried out in a manner similar to the inactivation of LDH, but with the E2 gene as the target for disruption.

In a further embodiment, a microorganism of the invention comprises a modification to inactivate the pyruvate formate lyase gene, thereby preventing/reducing the conversion of pyruvate to acetyl CoA and formate. Pyruvate formate lyase (PFL) is the "anaerobic counterpart" to pyruvate dehydrogenase (PDH) and converts pyruvate to acetyl CoA and formate (see FIG. 6). While acetyl CoA can be converted to ethanol via acetaldehyde dehydrogenase (AcHD), formate is an undesired side-product which has the potential to inhibit growth in ethanolgenic organisms.

PFL was chosen as a target for knockout in order to promote the metabolic flux towards ethanol production and to improve the redox balance of the remaining pathway to ethanol synthesis. An additional advantage of this work was the elimination of formate production. PFL activity can be inactivated via transposon insertion, gene deletion or partial gene deletion to produce a mutant which does not rely on antibiotic selection for the continuation of the altered phenotype. However, it is preferred if the pyruvate formate lyase gene is inactivated by the deletion of the gene sequence or a portion of the gene sequence. Deletion is preferred, as this avoids the difficulty of reactivation of the gene sequence which is often experienced when transposon inactivation is used. In this embodiment, it is preferred that the microorganism comprises both the lactate dehydrogenase inactivation and the up-regulation of the pyruvate dehydrogenase, so that, under anaerobic conditions, ethanol production is increased.

In a further preferred embodiment, the microorganism also comprises up-regulated pyruvate decarboxylase and/or alcohol dehydrogenase genes. The expression of these genes results in the production of enzymes which redirect the metabolism so that ethanol is the primary fermentation product. If the PDC gene is EC4.1.1.1, the gene will be heterologous and can be inserted in an expression cassette, as will be appreciated by the skilled person. If the PDC gene is EC1.2.4.1, it can be the homologous gene that is upregulated. The ADH gene may be heterologous or homologous. If the native gene is to be utilised, it may be upregulated by methods known in the art. Preferably, both PDC and ADH are expressed in the microorganism. The genes may be obtained from microorganisms that typically undergo anaerobic fermentation, including *Zymomonas* species, including *Zymomonas mobilis*.

Methods of the preparation and incorporation of a gene into microorganisms are known, for example in Ingram et al, Biotech & BioEng, 198; 58 (2 and 3): 204-214 and U.S. Pat. No. 5,916,787, the content of each being incorporated herein by reference. The gene may be introduced in a plasmid or integrated into the chromosome, as will be appreciated by the skilled person.

The thermophilic microorganism of the invention may be further modified to increase amylase gene expression compared to wild-type. Such modification is described in detail in WO2009/022158, the content of which is incorporated herein. This enables the microorganism to hydrolyse starch into glucose monomer units which can then be utilised as glycolytic substrates for the formation of pyruvate and subsequently ethanol. This modification therefore enables the increased production of ethanol from cheap, abundant, un-refined plant material.

Methods of increasing amylase expression and enzyme activity include the use of strong up-stream promoters to regulate transcription of the gene, incorporation of additional amylase genes that are expressed at a higher frequency than the native amylase gene, or the expression of a more active amylase gene. The term "strong promoter" is defined herein as a promoter that expresses the corresponding protein to a level greater than 0.5% of the soluble protein in a cell.

In a preferred embodiment, a heterologous amylase gene encodes α-amylase (α-1,4-glucan-4-glucanohydrolase, EC 3.2.1.1). It is preferred that the amylase gene is derived from the *Geobacillus* species, in particular *Geobacillus stearothermophilus*.

The coding sequence of the α-amylase gene has been elucidated and the techniques enabling isolation and amplification of the gene are well known in the art. In order to enable the microorganism of the invention to exhibit increased amylase expression compared to wild-type, it is preferred that the amylase gene is placed under the control of a strong promoter, which operates in low-aeration or anaerobic conditions that favour ethanol production by thermophilic microorganisms. The promoter is preferably an ldh promoter and may be autologous, but is preferably heterologous, and is most preferably derived from the same species as the amylase gene. Examples of suitable promoters include, but are not limited to, P_ldh from *G. stearothermophilus* NCA1503, P_ferrA from *G. stearothermophilus* DSM13240 and P_pfl from *B. cereus* ATCC14579.

In another embodiment of the invention, a series of different strong promoters are placed upstream of the amylase gene in order to further enhance expression. Examples of suitable strong promoters include, but are not limited to, the glyceraldehyde-3-phosphate promoter (P_GAPDH) and amylase promoter from *G. stearothermophilus* NCA 1503.

The nucleic acid sequence of P_ldh is also known and techniques for cloning and assembling the promoter sequence upstream of the amylase gene are known to the skilled person.

Figure 6:
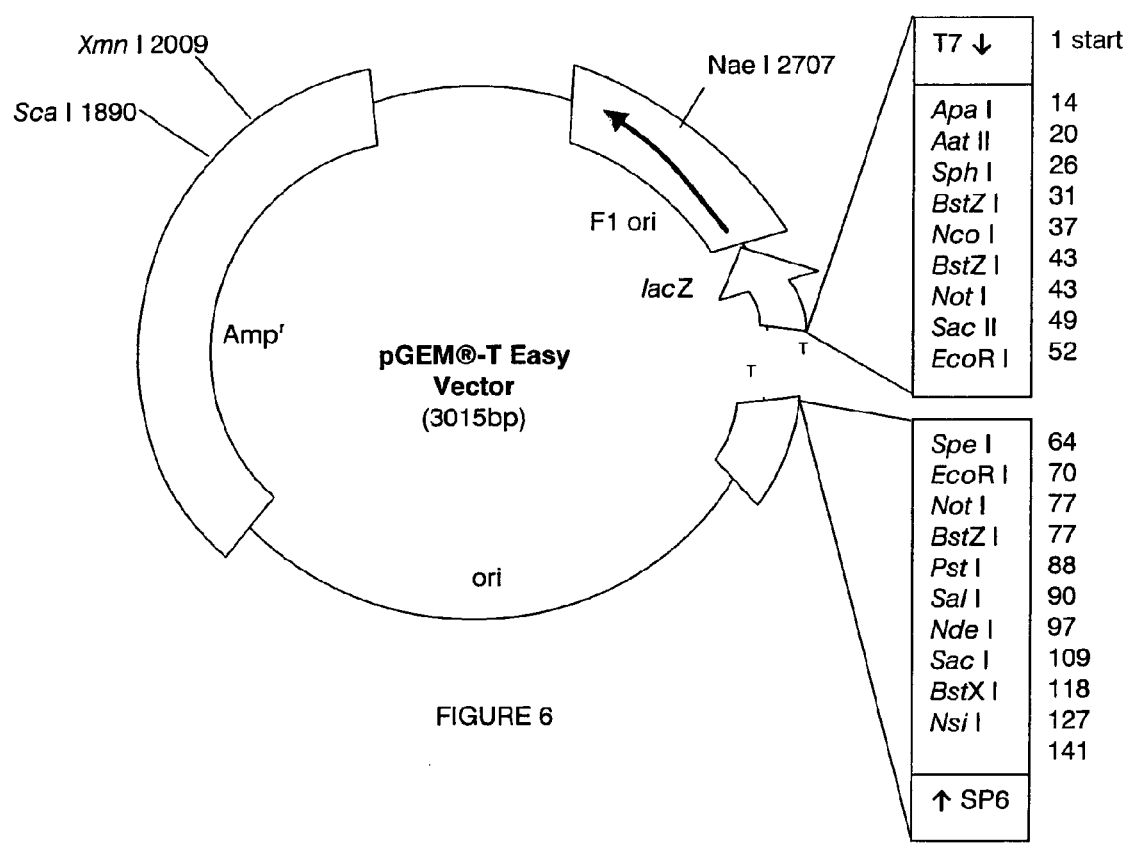
FIG. 6 illustrates the pGEM®-T Easy Vector.
Figure 7:
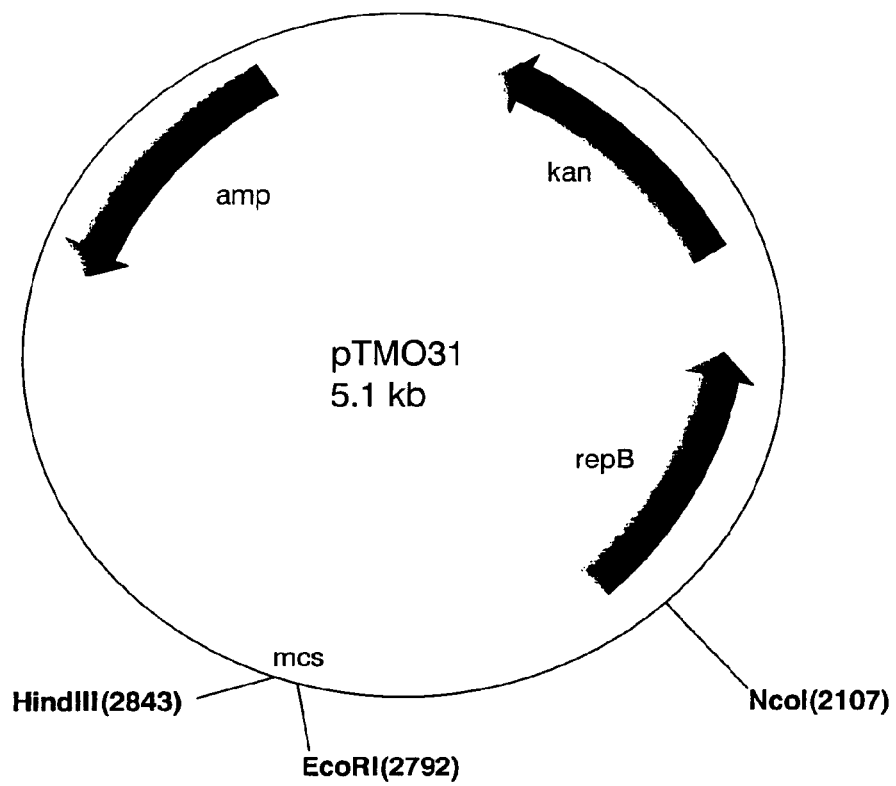
FIG. 7 illustrates the plasmid pTM031 (SEQ ID No. 3)

The promoter/amylase sequence can be cloned into a suitable plasmid or expression vector containing multiple restriction sites. There are numerous suitable expression vectors which are commercially available, such as the pGEM®-T Easy Vector (FIG. 6). Restriction enzymes can be used to excise the P_ldh/amylase construct as a specific fragment which can be ligated into the corresponding restriction site in a temperature-sensitive plasmid such as pTMO31 (FIG. 7, SEQ ID No. 3) able to use a pyruvate formate lyase knock-out plasmid. The plasmid construct comprising the amylase gene/ldh promoter can then be electroporated into the microorganism of the invention with subsequent homologous recombination with genomic DNA. Chromosomal integrants can be selected for on the basis of their resistance to antibacterial agents, such as ampicillin or kanamycin. Amylase activity can also be visualised as zones of starch clearing, for example on plate assays. The culture media may preferably comprise at least 1% w/v starch, preferably at least 10% w/v starch, and most preferably at least 20% w/v starch. The starch may be soluble or insoluble (e.g. grain starch).

An embodiment of the present invention will now be described, with reference to the accompanying drawings, in the following example. The present invention is exemplified but not limited, by the example.

Example

Figure 8:
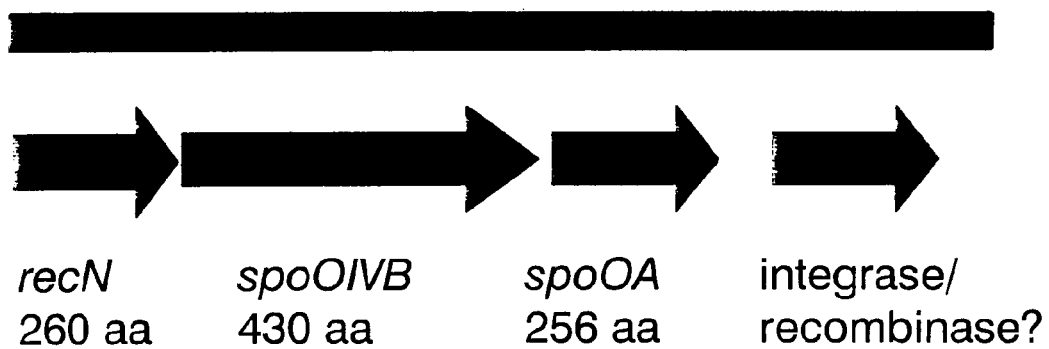
FIG. 8 illustrates schematically the organisation of spo0A and surrounding genes from a 4480 bp sequence read of genomic DNA isolated from *G. thermoglucosidasius*.

Two different Spo0A knock-out constructs were developed to take account of other sporulation genes adjacent to the target spo0A which could be transcriptionally affected upon out-of-frame spo0A disruption, as illustrated in FIG. 8.

Figure 9:
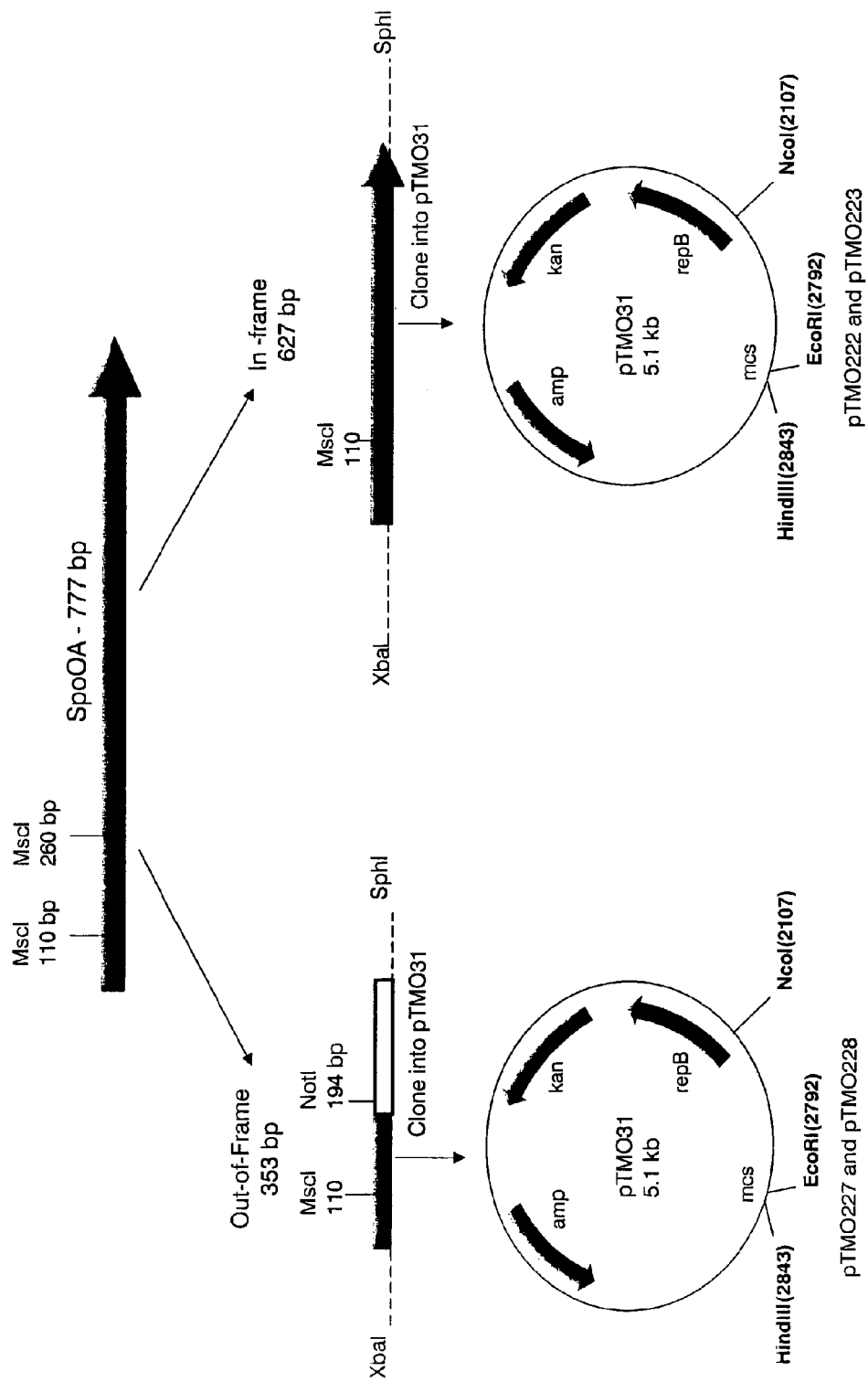
FIG. 9 outlines the two approaches to disrupting the spo0A gene.

Thus an out-of-frame and an in-frame knockout cassette were produced as outlined in FIG. 9. The out-of-frame cassette was generated by the removing of a 429 bp region of the spo0A gene and replacing it with an engineered NotI restriction site to enable hybridisation of primers for PCR amplification of fragments comprising spo0A deletions, while the in-frame cassette was constructed by removing the naturally occurring 150 bp MscI-MscI fragment.

The resulting fragments were cloned into pTM031, which is a 5.1 kb plasmid derived from an EcoRI/SnaBI pUB110 fragment insert into pUC19. The plasmid map of pTM031 is illustrated in FIG. 3 and the nucleic acid sequence of pTM031 corresponds to SEQ ID No. 7. Nucleotides 1-239, 2634-2791 and 2848-5082 are derived from pUC19, nucleotides 240-2633 are derived from pUB110 and the remaining nucleotides (2792-2848) correspond to the multiple cloning site (MCS).

The resulting plasmids were then used to transform *Geobacillus* microorganisms which incorporated other modifications as set out below. Methods of transformation, primary integration and stabilisation via selection of double crossover mutants were employed in a variety of strain backgrounds, as detailed below.

*Geobacillus thermoglucosidasius* Strain Backgrounds

| Strain name | Modification(s) |
|---|---|
| TM89 | ldh⁻ |
| TM242 | ldh⁻, pdh_up, pfl⁻ |
| TM266 | ldh⁻, pdh_up, P_ldh(Ste), pfl⁻ |
| TM379 | ldh⁻, pdh_up, P_pfl(11955), pfl⁻ |
| TM333 | ldh⁻, pdh_up, pfl⁻, P_ldh(NCA)/amyS(DSM22) |

Results
Generation of Spo0A Mutants in TM242

A total of 20 presumptive primary integrants (4 in-frame and 16 out-of-frame) of TM242 (NCIMB Accession No. 41589) were sub-cultured through two rounds of growth in 2TY medium at 60° C. Cells from each of these cultures were plated onto TGP medium and subsequently replicated onto TGP containing kanamycin at a final concentration of 12.5 µg/ml. A total of 13 (5 in-frame, 8 out-of-frame) kanamycin-sensitive strains representing putative double cross-over mutants with a disrupted spo0A gene were identified.

Difco Sporulation Medium (DSM), made according to the following recipe, was used to demonstrated the ability of the mutants to sporulate. Testing was conducted before and after heat treatment to kill vegetative cells.

Difco Sporulation Medium (DSM)

|  | Per liter |
|---|---|
| Bacto nutrient broth (Difco) | 8 g |
| 10% (w/v) KCl | 10 ml |
| 1.2% (w/v) MgSO$_4$•7H$_2$O | 10 ml |
| 1M NaOH | ~1.5 ml (pH to 7.6) |

The volume is adjusted to 1 litre with ddH$_2$0 and the pH is adjusted to 7.6. The solution is then autoclaved and allowed to cool to 50° C. The following sterile solutions (and antibiotics if required) are added prior to use:

| 1M Ca(NO$_3$)$_2$ | 1 ml |
|---|---|
| 0.01M MnCl$_2$ | 1 ml |
| 1 mM FeSO$_4$ | 1 ml |

A dilution series for TM242 and one of its out-of-frame Spo0A-negative offspring, TM443, were plated on TGP both before and after both strains were heat treated at 90° C. for 30 minutes. When not subjected to heat treatment, there was comparable growth between TM242 and TM443 at each dilution. However, after heat treatment there was a clear difference. While TM242 still showed growth at each dilution, albeit less than before heat treatment, there was no growth on the TM443 plate—even in the neat culture patch—indicating that TM242 can sporulate but TM443 cannot. To date, everything that has been done to make these strains sporulate has indicated that they are not capable of doing so.

Figure 10:
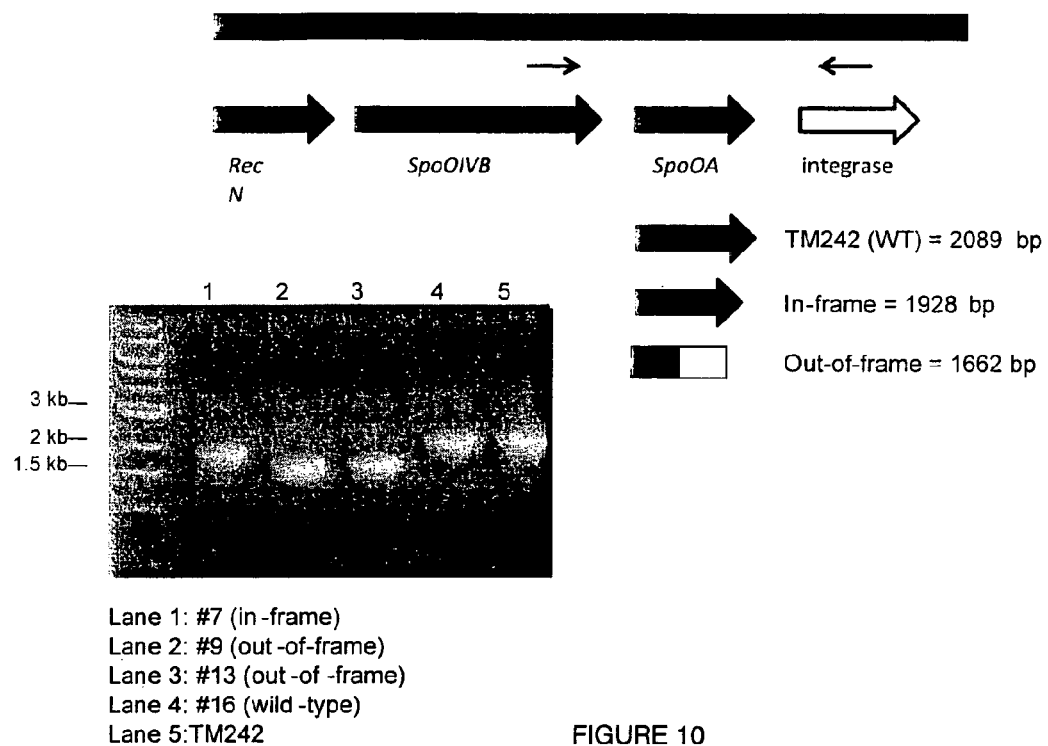
FIG. 10 illustrates the expected PCR product sizes of spo0A knock-out compared with the original spo0A gene.

In addition, genomic DNA was isolated from the TM242 double cross-over mutants and used as templates in PCR reactions together with the primers O/Spo0A1bF and O/Spo0A2R which flank the spo0A region, see FIG. 10. PCR products were generated for each template and analysed by specific restriction enzyme digestion. The DNA fragments generated by these restriction digests are consistent with two of the strains representing out-of-frame mutants of the spo0A gene and one strain representing an in-frame deletion. Southern hybridisation analysis confirmed these results. Therefore, it can be concluded that a) the target spo0A gene has been knocked-out; and b) this has resulted in loss of sporulation in these strains.

Fermentation Characteristics of Spo0A Negative Strains

The improved fermentation characteristics of Spo0A negative strains at lower sugar concentrations were demonstrated using urea salts media (USM) made according to the following recipe:

Urea Salts Media (USM)

|  | Final Concentration |
|---|---|
| NaH$_2$PO$_4$•2H$_2$O | 10 mM |
| K$_2$SO$_4$ | 10 mM |
| Citric acid | 2 mM |
| MgSO$_4$•7H$_2$O | 1.25 mM |
| CaCl$^2$•2H$_2$O | 0.02 mM |
| Na$^2$MoO$^4$•2H$_2$O | 1.65 mM |
| Urea | 50 mM |
| ZnSO$_4$•7H$_2$O | 25 µM |
| FeSO$_4$•7H$_2$O | 100 µM |
| MnSO$_4$•H$_2$O | 50 µM |
| CuSO$_4$•5H$_2$O | 5 µM |
| CuSO$_4$•7H$_2$O | 10 µM |
| NiSO$_4$•6H$_2$O | 16.85 µM |
| H$_3$BO$_3$ | 6.5 µM |

The above components were added to deionised water and the following filter-sterilised reagents were added:

| Biotin | 12.5 µM |
|---|---|
| Yeast extract | 0.5% w/v (after autoclaving) |

As shown in Tables 2A and 2B, it appears that under controlled fermentation conditions (1 L batch, USM with 3% w/v glucose, 1% w/v yeast extract, pH 6.8, 60° C., aeration regime: 1 L/min and 600 rpm until OD>5.0 then 0.2 L/min and 300 rpm) the out-of-frame mutant TM444 is able to consume sugar faster than TM242 and the in-frame mutants TM448 and TM450 perform less well.

TABLE 2A

| Strain | Spo⁻ | Aeration Switch Hrs | OD | Complete sugar consumption/ hours | Max OD$_{600}$ | Glucose/ mM | Pyruvate/ mM |
|---|---|---|---|---|---|---|---|
| TM242 |  | 2.5 | 5.6 | 7.5 | 9.8 | 0.0 | 1.0 |
| TM443 | ✓ o | 2.3 | 5.8 | 6.7 | 8.6 | 0.0 | 0.0 |
| TM444 | ✓ o | 2.2 | 5.6 | 5.6 | 9.0 | 0.0 | 0.0 |
| TM448 | ✓ i | 3.0 | 5.3 | 9.8 | 7.2 | 0.0 | 1.0 |
| TM450 | ✓ i | 3.8 | 5.7 | 9.9 | 8.3 | 0.0 | 3.0 |

NB: 'i' denotes in-frame mutant, 'o' denotes out-of-frame mutant

TABLE 2B

| Strain | Lactate/ mM | Formate/ mM | Actate/ mM | Ethanol/ mM | Ethanol yield post aeration switch/gg⁻¹ | Overall ethanol yield/ gg⁻¹ |
|---|---|---|---|---|---|---|
| TM242 | 10.0 | 0.0 | 13.0 | 314.0 | 0.44 | 0.42 |
| TM443 | 16.0 | 0.0 | 15.0 | 300.0 | 0.44 | 0.40 |
| TM444 | 13.0 | 0.0 | 15.0 | 303.0 | 0.46 | 0.42 |
| TM448 | 6.0 | 0.0 | 21.0 | 243.0 | 0.42 | 0.33 |
| TM450 | 5.0 | 0.0 | 28.0 | 252.0 | 0.43 | 0.35 |

As shown in Table 2B, the ethanol yield post-aeration switch of TM443 is equal to that of the parent strain TM242, whilst for TM444 is slightly improved. More importantly however, as shown in Table 2A, at these lower sugar concentrations (3% w/v glucose) TM443 and TM444 complete sugar consumption significantly faster than TM242. This is an advantageous characteristic in a commercial fermentation process. It is worth noting that in these fermentations, at 3% (w/v) sugar concentrations, TM444 and TM443 are able to utilise sugar more quickly. This is beneficial, as it allows more fermentation batches to be run over time, resulting in significant increases in overall ethanol production.

Figure 11:
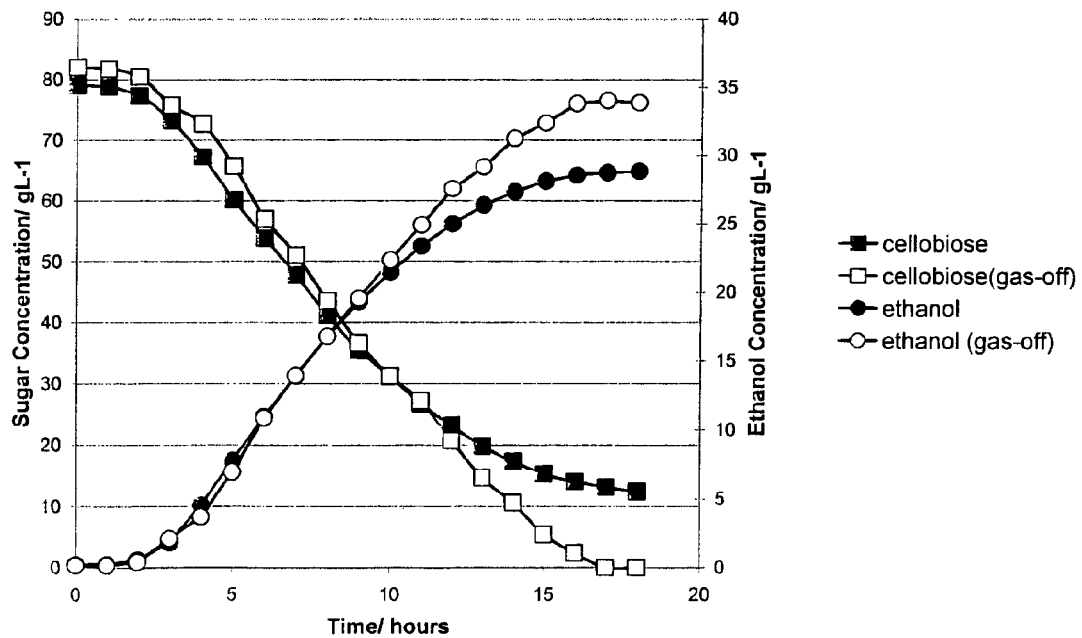
FIG. 11 is a graph showing alterations in the fermentation characteristics of TM242 in media comprising 8% w/v cellobiose and 2% yeast extract when ethanol vapour is partitioned from the fermentation broth ("gas-off") and when it is not partitioned from the broth.

The enhanced ethanol tolerance of TM444 compared to TM242 is illustrated in FIG. 11. It has been found that fermentation of 8% w/v cellobiose by TM242 could proceed to completion only if the ethanol produced during fermentation was partitioned into the vapour phase and remove from the fermentation broth. As shown in FIG. 11, when ethanol vapour was removed from the fermenter during fermentation (i.e. "gas-off") TM242 was able to utilise all of the cellobiose by the end of the fermentation, and the resulting total concentration of ethanol produced was increased, compared with fermentation without the removal of ethanol vapour from the broth. Interestingly, it was not necessary to portion off ethanol vapour in order for the same fermentation media to be fully fermented by TM444. This is because TM444 exhibits improved ethanol tolerance.

Figure 12A:
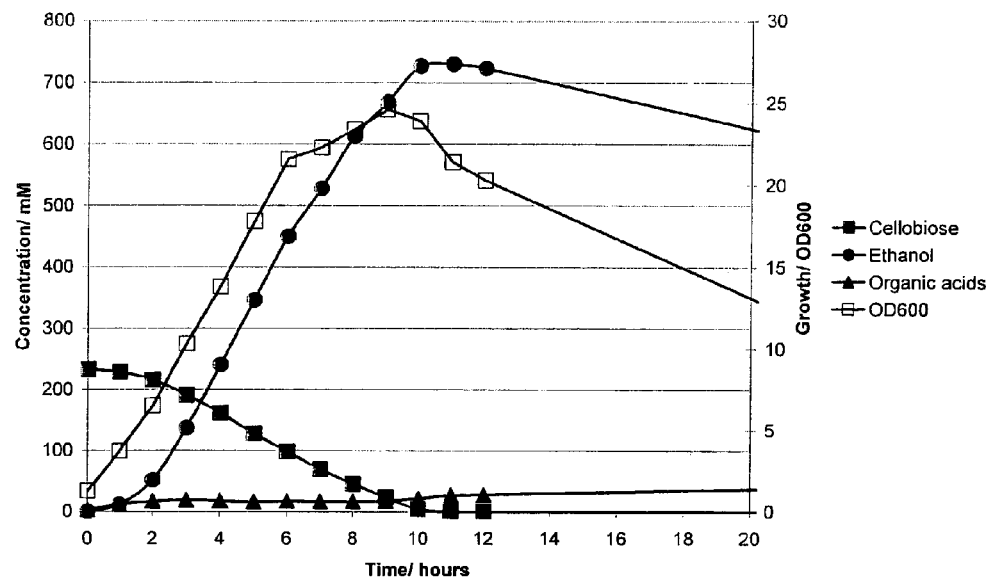
FIG. 12a is a graph showing the fermentation characteristics of TM242 in media comprising 8% w/v cellobiose and 2% w/v yeast extract and FIG. 12b shows the fermentation characteristics of TM444 in the same media.
Figure 12B:
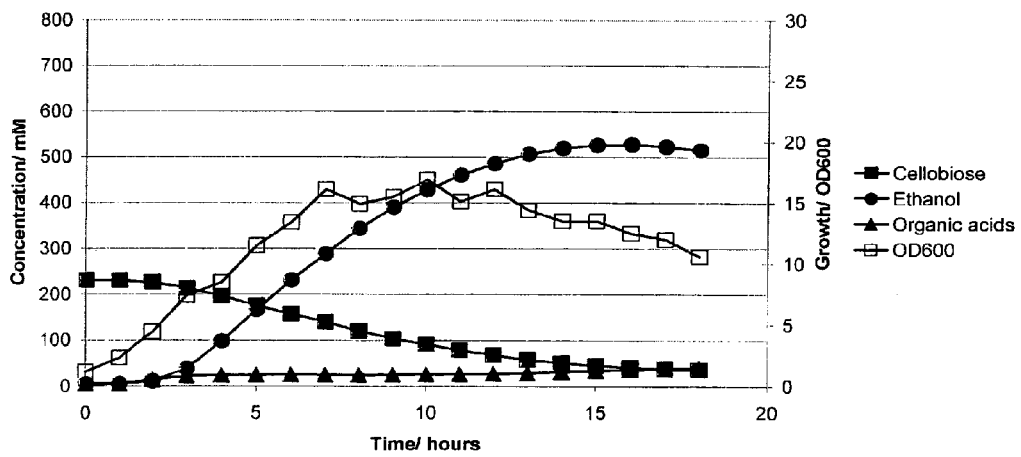

The improved fermentation characteristics of TM444 are further illustrated in FIGS. 12a and 12b, which show the fermentation curves for TM242 and TM444 respectively in media comprising 8% w/v cellobiose and 2% w/v yeast extract. By comparing the two graphs, it can be seen that, at elevated sugar concentrations, TM444 completed sugar consumption in approximately 10 hours, whilst some sugar still remained after 18 hours (i.e. the end of fermentation) when TM242 was used. Furthermore, the ethanol peak for TM242 shown in FIG. 12a is significantly lower than the ethanol peak for TM444 shown in FIG. 12b (527 mM for TM242 compared with 729 mM for TM444).

Therefore, it can be concluded from the data presented in FIGS. 11, 12a and 12b that, at elevated sugar concentrations, the sporulation-deficient mutant strains of the invention exhibit improved ethanol tolerance, an increased rate of sugar consumption and an increase in overall ethanol yield, compared to the parent strain.

Generation of Spo0A Mutants in TM333

In further work, TM333 presumptive primary integrants of the Spo0A gene were sub-cultured through two successive rounds of growth in 2TY broth without antibiotic. Cells from the final round of sub-culturing were serially diluted and grown on TGP medium. Kanamycin-sensitive colonies representing potential double crossovers were identified by replica plating. Through a combination of PCR analysis and testing for sporulation, TM486, an out-of-frame sporulation-deficient derivative of TM333 has been identified as a useful strain for ethanol production. The TM486 strain has been deposited at NCIMB Ltd, Ferguson Building, Craibstone Estate, Bucksburn, Aberdeen AB21 9YA and has the Accession No. NCIMB 41587.

Since this strain comprises the amyS gene present in the parent strain TM333, it provides the combined advantages of increased ethanol tolerance, rapid feedstock consumption and improved ethanol production that are associated with the spo0A mutation, together with the capacity to efficiently metabolise starch-based feedstock due to increased amylase activity.

The content of all of the publications referred to in the description is incorporated herein by reference.

The invention claimed is:

1. An isolated thermophilic microorganism comprising a modification that decreases sporulation compared with wild-type, wherein the modification inactivates the native stage 0 sporulation protein A (spo0A) gene, and wherein the microorganism is a *Geobacillus thermoglucosidasius*.

2. The microorganism according to claim 1, wherein the modification comprises the deletion of at least a portion of the spo0A gene.

3. The microorganism according to claim 2, wherein the modification further comprises replacing the deleted portion of the spo0A gene with DNA encoding a restriction site.

4. The microorganism according to claim 3, wherein the restriction site is a NotI restriction site.

5. The microorganism according to claim 1, further comprising a modification that inactivates the native lactate dehydrogenase gene.

6. The microorganism according to claim 5, wherein the lactate dehydrogenase gene, or a portion thereof, has been deleted.

7. The microorganism according to claim 5, wherein the microorganism does not comprise an integration element in the lactate dehydrogenase gene.

8. The microorganism according to claim 1, further comprising a modification that inactivates the native pyruvate formate lyase gene.

9. The microorganism according to claim 8, wherein the pyruvate formate lyase gene, or a portion thereof, has been deleted.

10. The microorganism according to claim 1, further comprising a modification that up-regulates the pyruvate dehydrogenase gene.

11. The microorganism according to claim 10, wherein a gene promoter is inserted upstream of the pyruvate dehydrogenase gene, and wherein the promoter operates under anaerobic conditions.

12. The microorganism according to claim 1, further comprising a modification that enhances pyruvate decarboxylase activity.

13. The microorganism according to claim 12, wherein the modification inactivates the dihydrolipoamide transacetylase gene (EC 2.3.1.12).

14. The microorganism according to claim 12, wherein the dihydrolipoamide transacetylase gene, or a portion thereof, is deleted.

15. The microorganism according to claim 1, wherein the microorganism comprises a heterologous pyruvate decarboxylase gene.

16. The microorganism according to claim 1, wherein the microorganism comprises a heterologous alcohol dehydrogenase gene.

17. The microorganism according to claim 1, wherein the microorganism is identified as TM443 (Accession Number 41591) or TM444 (Accession Number 41588).

18. The microorganism according to claim 1, wherein the microorganism comprises a heterologous amylase gene under the control of a promoter which operates in anaerobic conditions.

* * * * *